(12) United States Patent
Hashimoto et al.

(10) Patent No.: US 6,962,082 B2
(45) Date of Patent: Nov. 8, 2005

(54) DEVICE AND METHOD FOR ACOUSTIC DIAGNOSIS AND MEASUREMENT BY PULSE ELECTROMAGNETIC FORCE

(75) Inventors: Mitsuo Hashimoto, Sagamihara (JP); Masanori Takanabe, Yokohama (JP)

(73) Assignee: Amic Co., Ltd., Yokohama (JP)

( * ) Notice: Subject to any disclaimer, the term of this patent is extended or adjusted under 35 U.S.C. 154(b) by 53 days.

(21) Appl. No.: 10/416,153

(22) PCT Filed: Nov. 7, 2001

(86) PCT No.: PCT/JP01/09742

§ 371 (c)(1),
(2), (4) Date: May 14, 2003

(87) PCT Pub. No.: WO02/40959

PCT Pub. Date: May 23, 2002

(65) Prior Publication Data

US 2004/0025593 A1 Feb. 12, 2004

(30) Foreign Application Priority Data

Nov. 17, 2000 (JP) ...................................... 2000-351879
Mar. 12, 2001 (JP) ...................................... 2001-068078

(51) Int. Cl.$^7$ ............................................. G01N 29/04
(52) U.S. Cl. .............................. 73/579; 73/643; 73/594
(58) Field of Search .......................... 73/582, 587, 588, 73/643, 594, 579, 657

(56) References Cited

U.S. PATENT DOCUMENTS 4,633,715 A * 1/1987 Monchalin .................. 73/657
5,902,935 A * 5/1999 Georgeson et al. ........... 73/801
2004/0123665 A1 * 7/2004 Biodgett et al. .............. 73/579

OTHER PUBLICATIONS

J. Krautkramer et al., Ultrasonic Testing of Materials, 3$^{rd}$ Ed. (1983), Springer–Verlag, New York, pp. 157–161.*
Patent Abstracts of Japan, Publication No. 2001-194347, dated Jul. 19, 2001.
Patent Abstracts of Japan, Publication No. 7-218477, dated Aug. 18, 1995.

* cited by examiner

*Primary Examiner*—John E. Chapman
(74) *Attorney, Agent, or Firm*—Westerman, Hattori, Daniels & Adrian, LLP

(57) ABSTRACT

The invention provides an acoustic diagnosis/measurement apparatus/method using a pulse of electromagnetic force, capable of non-destructively and precisely diagnosing or measuring corrosion, adhesion, the cover depth, and/or the diameter of a reinforcing iron rod in a structure made of reinforced concrete. A coil 12 is attached to a surface of a structure 11 including a conductor 11*a* and a non-conductive material 11*b* covering the conductor 11*a*. A current pulse is applied to the coil 12 thereby generating a magnetic field pulse. The magnetic field pulse causes an eddy current to be induced in the conductor 11*a*. The conductor 11*a* is oscillated by interaction between the eddy current and the magnetic field pulse. As a result, an acoustic signal is generated by the conductor 11*a* and the acoustic signal is converted into an eclectic signal by an acoustic transducer 14 disposed to the surface of the structure 11. The resultant electric signal is measured by a measurement unit 15 to diagnose/measure the location of the conductor 11*a* or the state of the structure 11.

20 Claims, 28 Drawing Sheets

FIG. 1
(a)
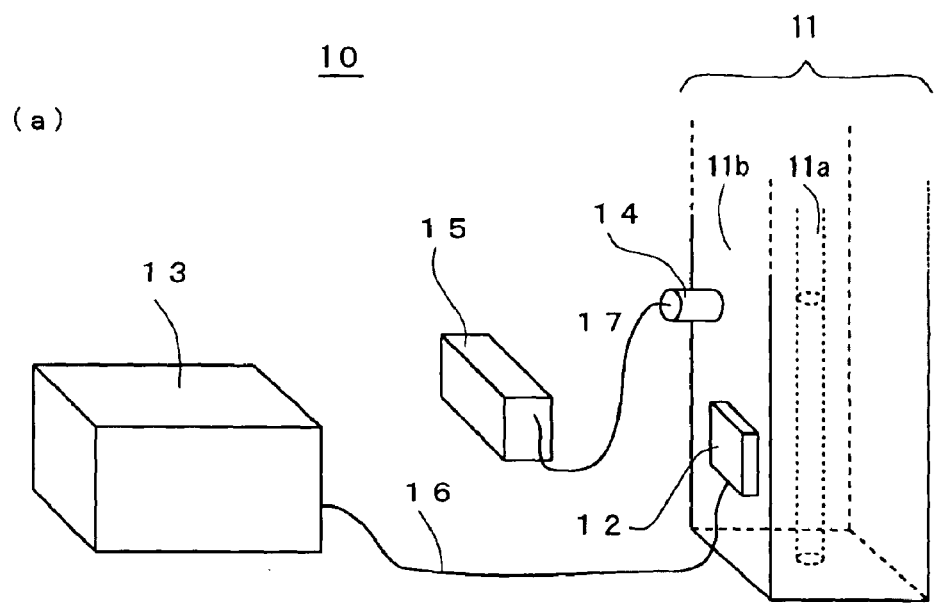
(b)
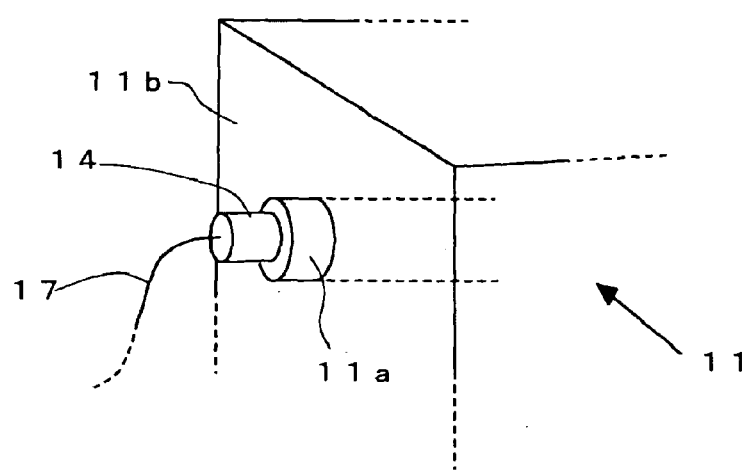

FIG. 3
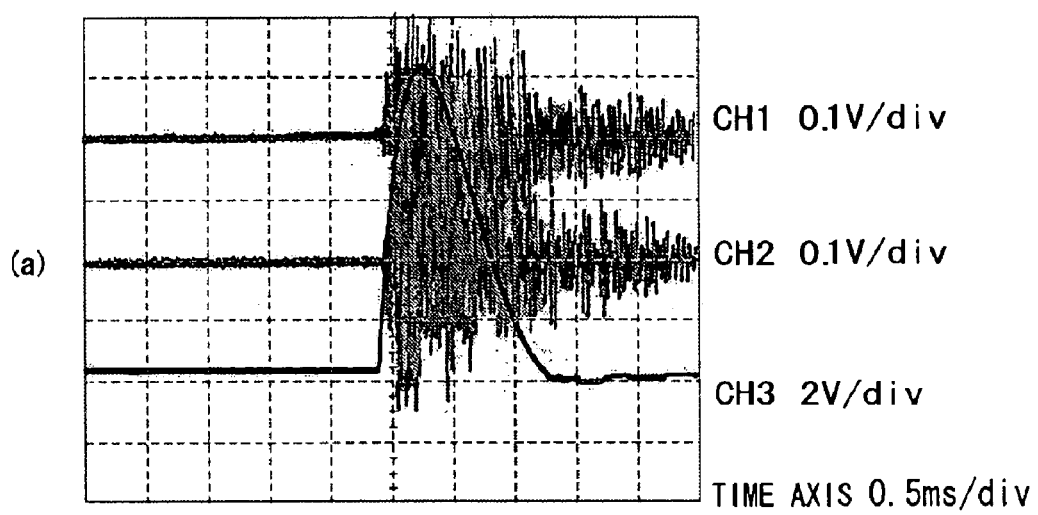
(a)
CH1 0.1V/div
CH2 0.1V/div
CH3 2V/div
TIME AXIS 0.5ms/div
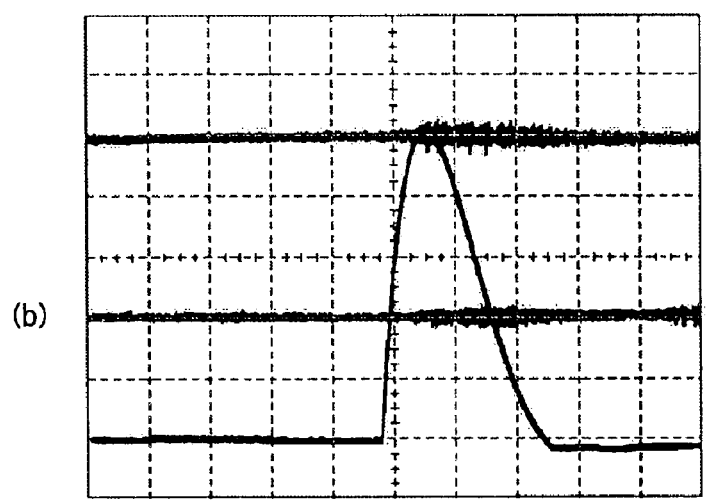
(b)

F I G. 4
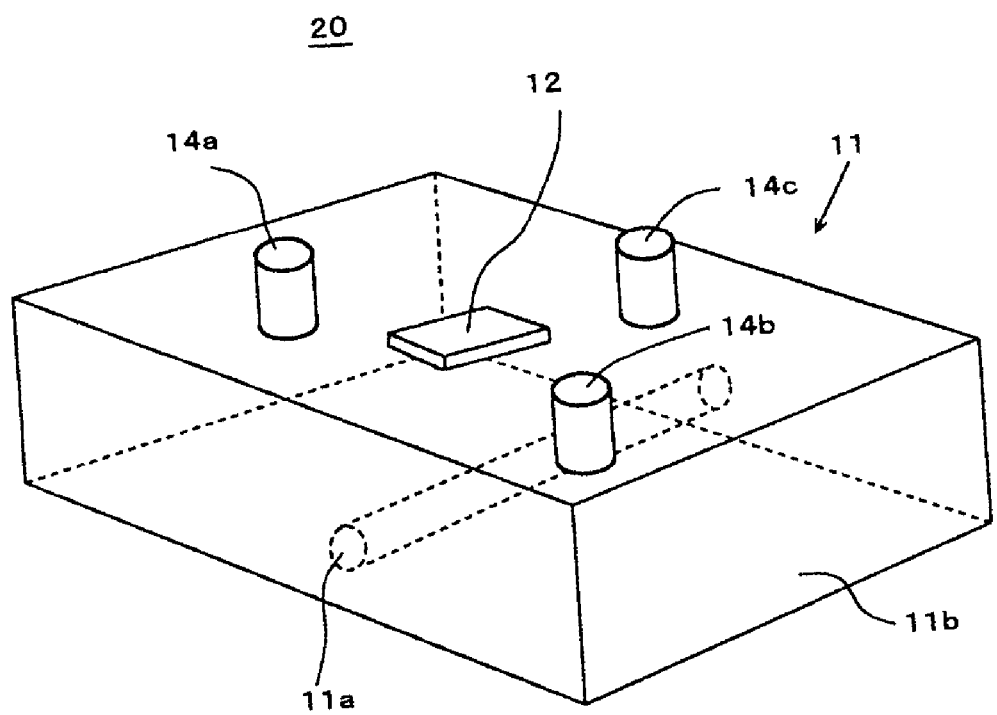

F I G. 6
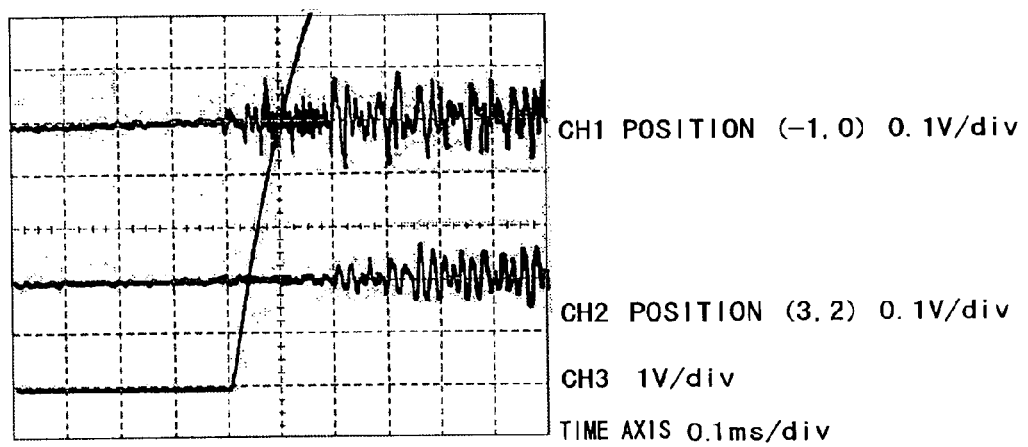

FIG. 9
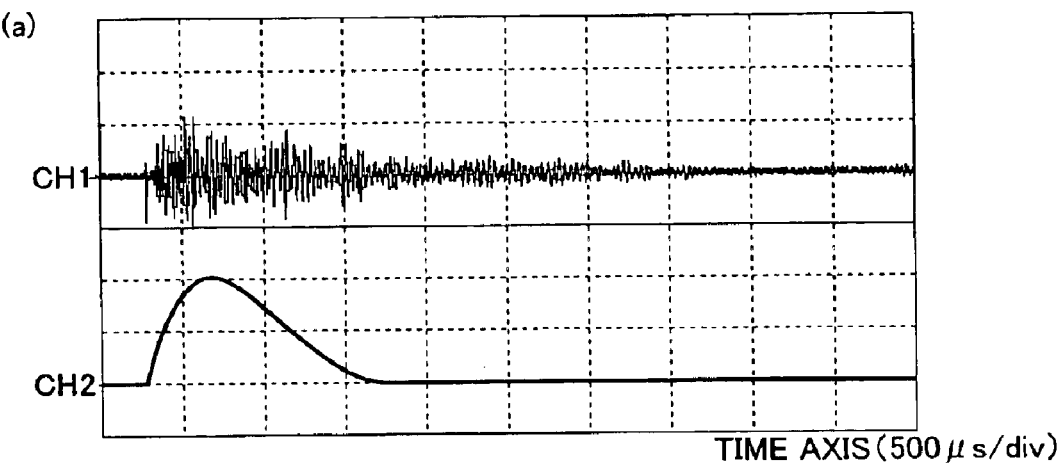
(a)
TIME AXIS (500 μs/div)
CH1 WAVEFORM RECEIVED BY THE AE SENSOR  Gain 40+10dB
(200mV/div)
CH2 PULSE WAVEFORM  PULSE WIDTH 1500 μs
(5V/div)  CURRENT 1000A
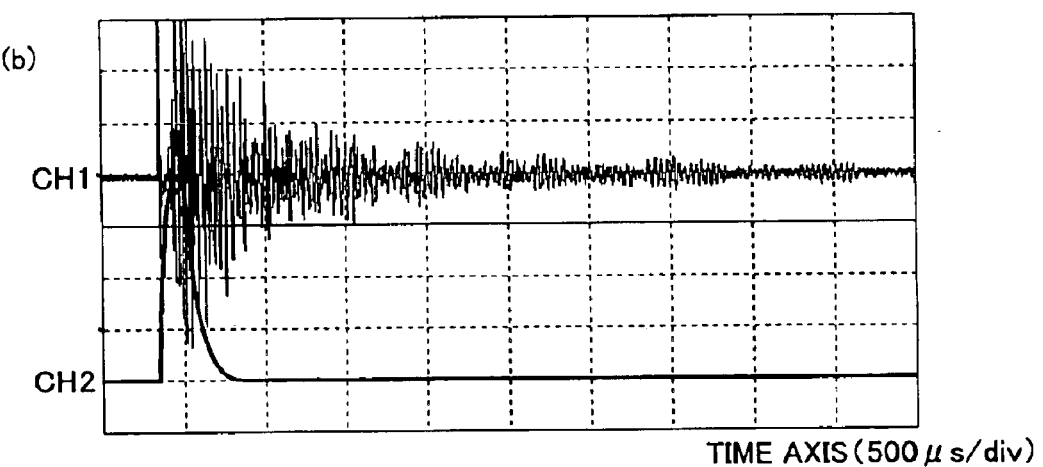
(b)
TIME AXIS (500 μs/div)
CH1 WAVEFORM RECEIVED BY THE AE SENSOR  Gain 40+10dB
(200mV/div)
CH2 PULSE WAVEFORM  PULSE WIDTH 350 μs
(5V/div)  CURRENT 2000A

FIG. 12

| TEST BLOCK NO. | SHAPE FACTOR | CREST FACTOR |
|---|---|---|
| (A) | 1.72 | 7.62 |
| (B) | 1.47 | 5.10 |
| (C) | 1.24 | 3.16 |

FIG. 13
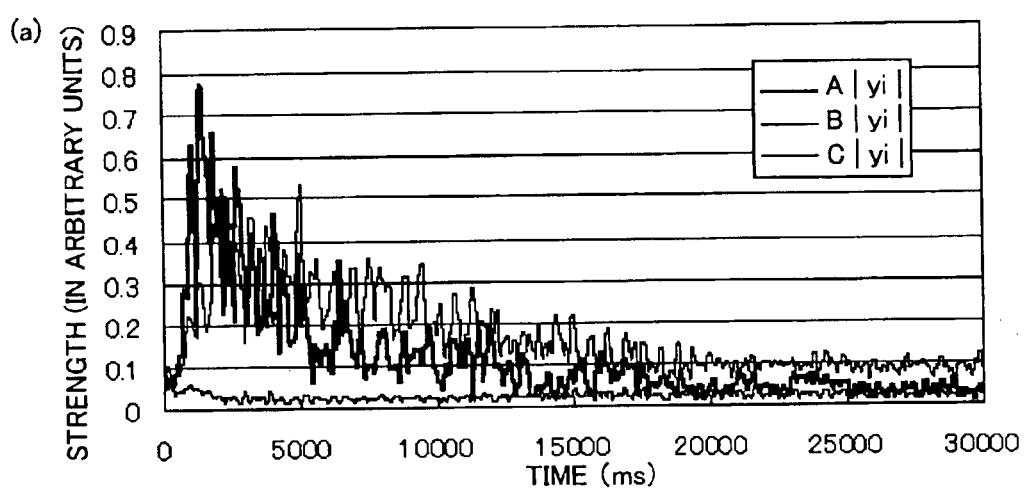
(a)
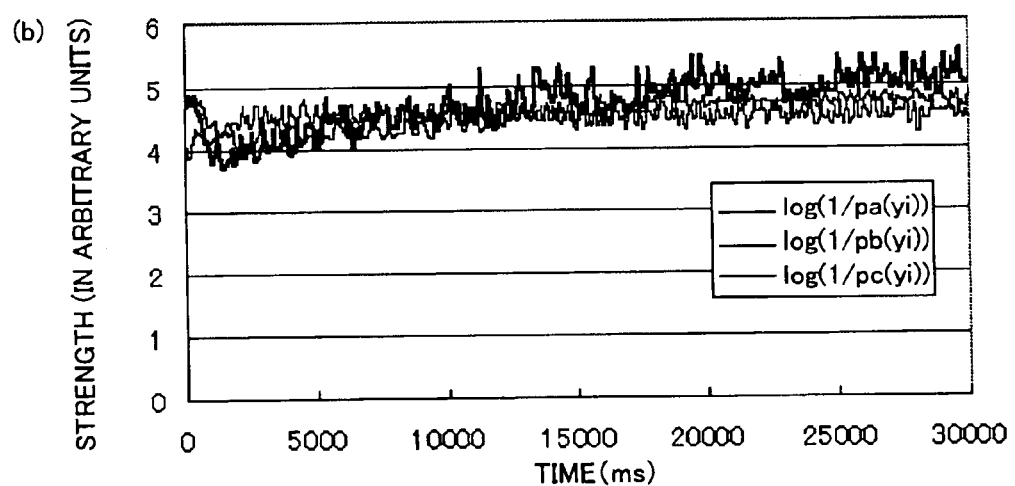
(b)

FIG. 14
(a)
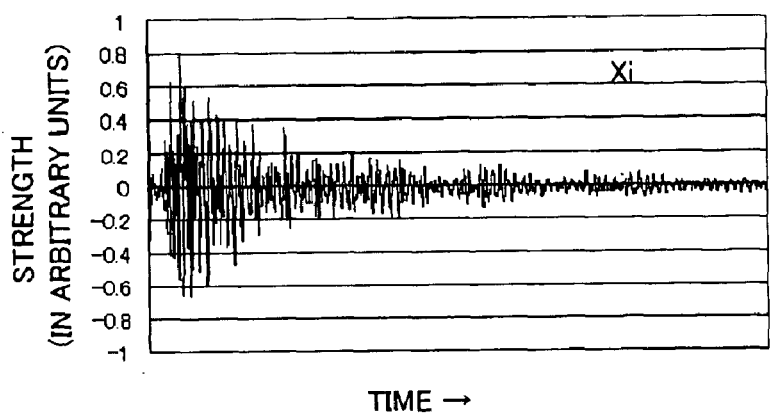
(b)
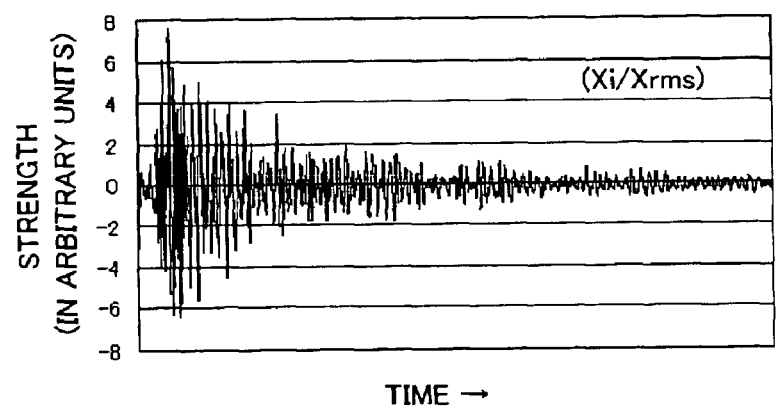
(c)
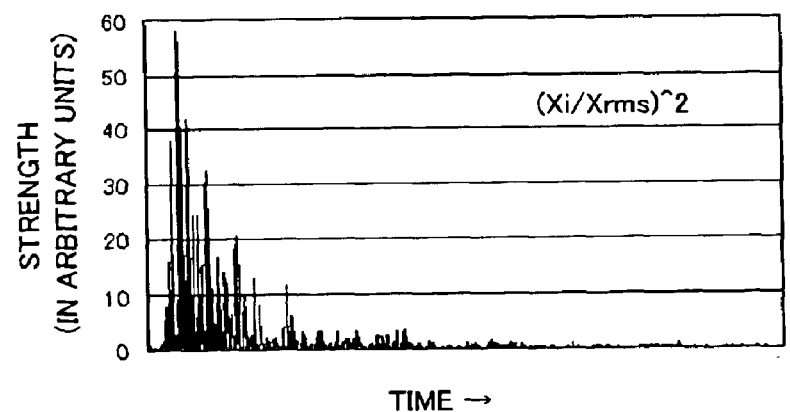

FIG. 16
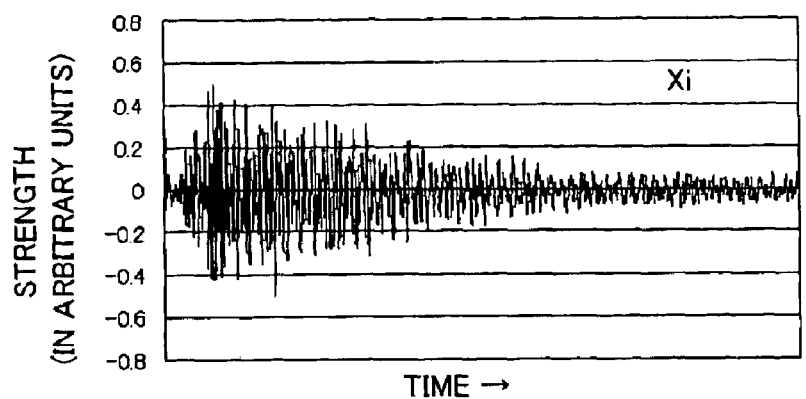
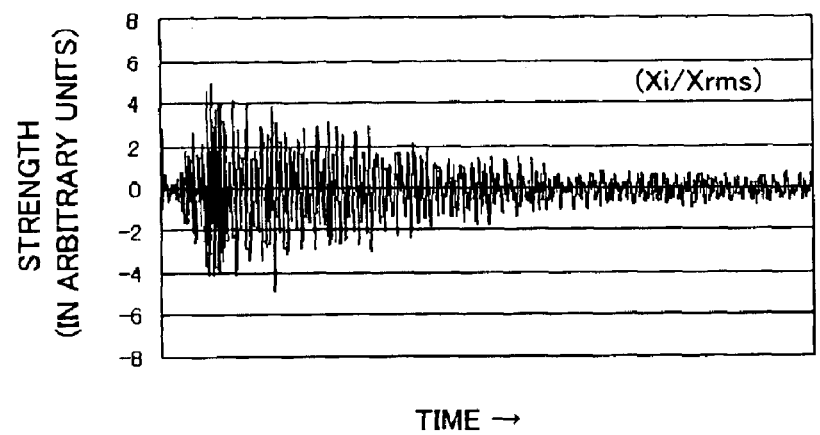
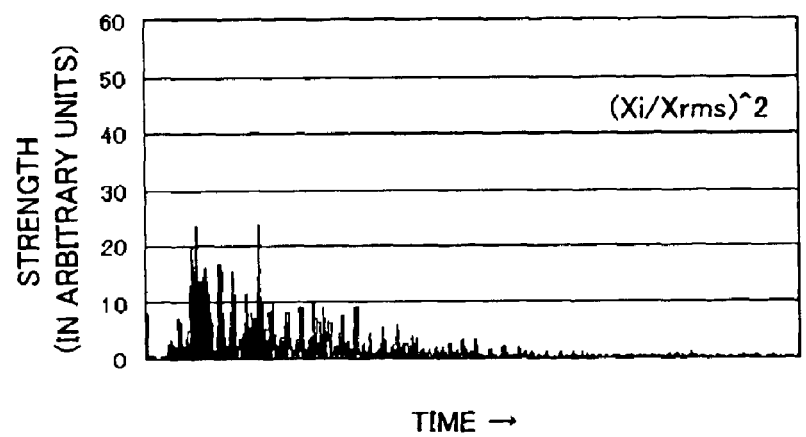

F I G. 1 7
(a) 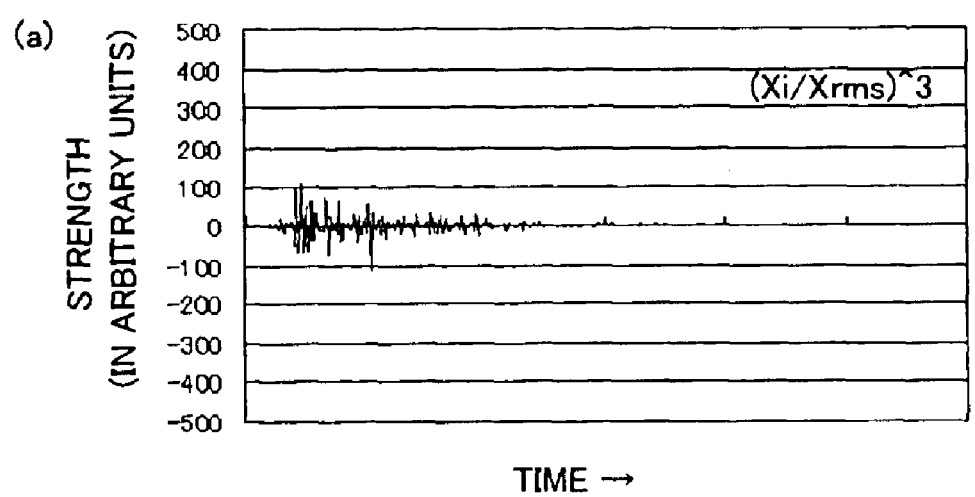
(b) 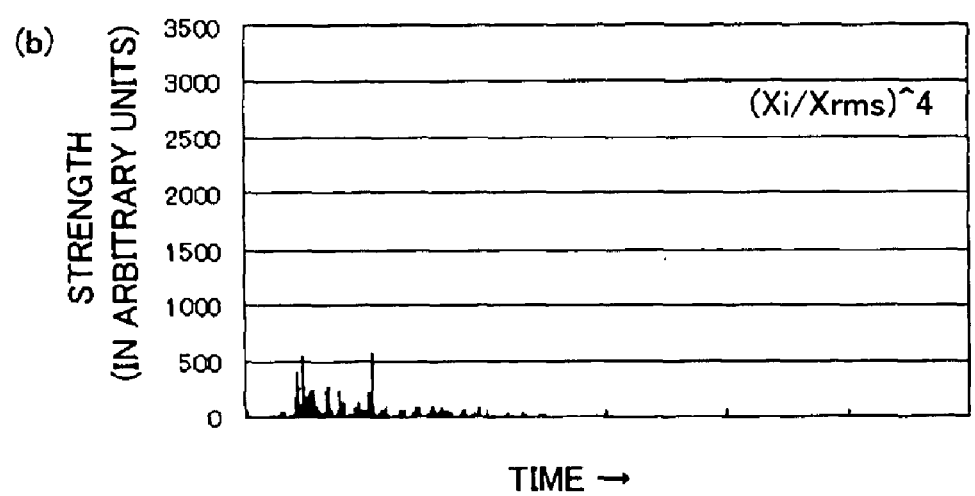

FIG. 18
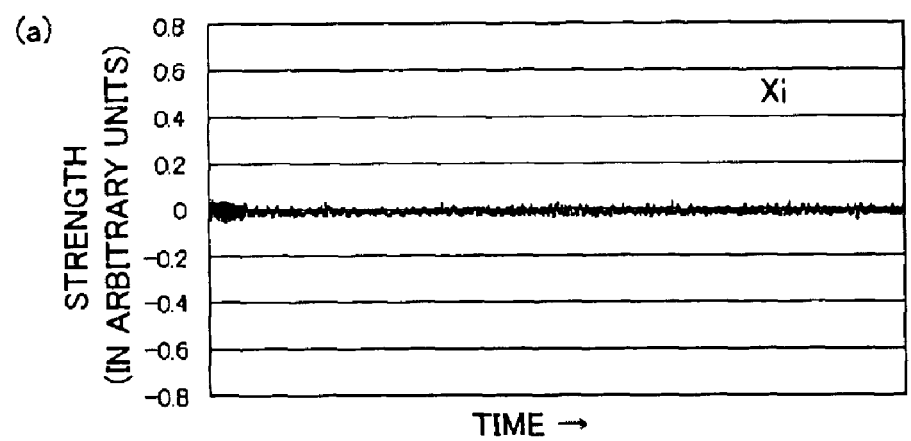
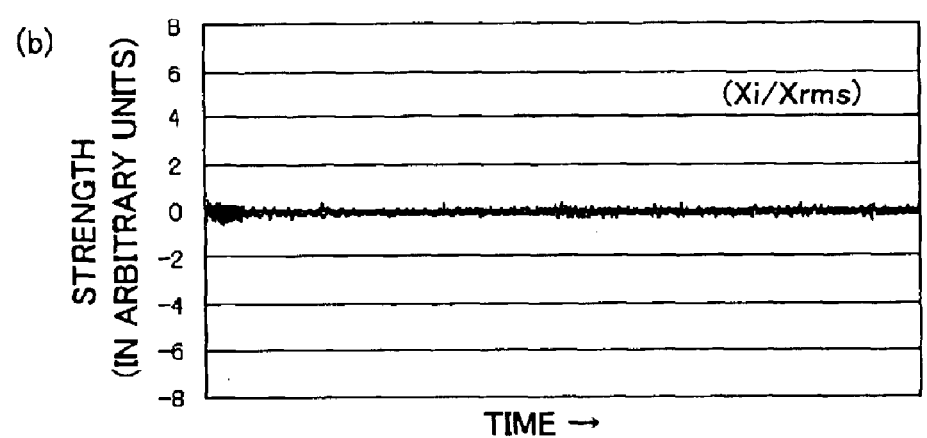
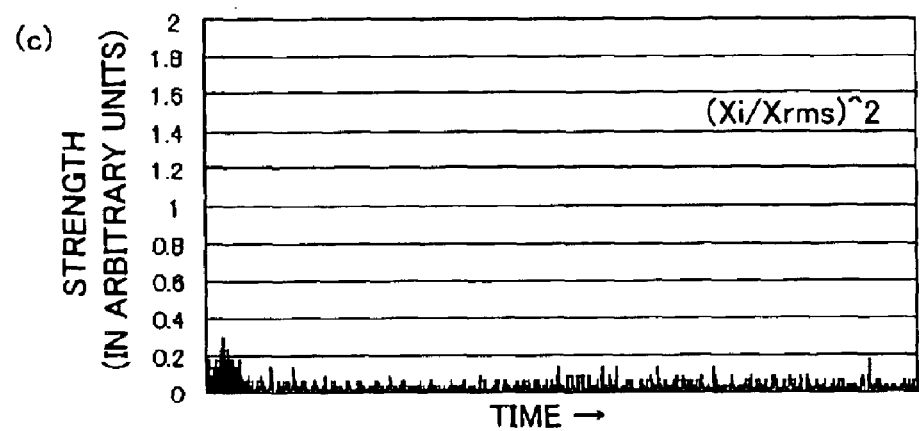

FIG. 19
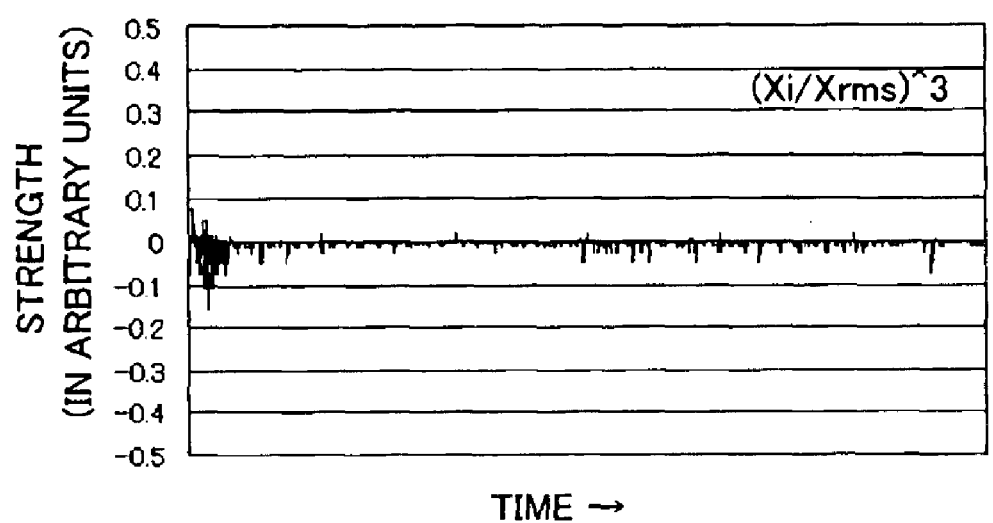
(a)
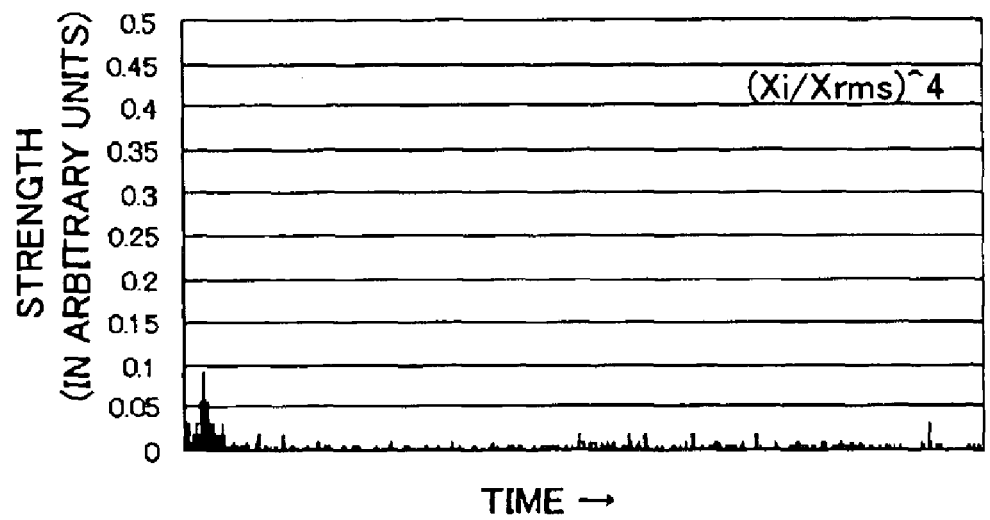
(b)

FIG. 22
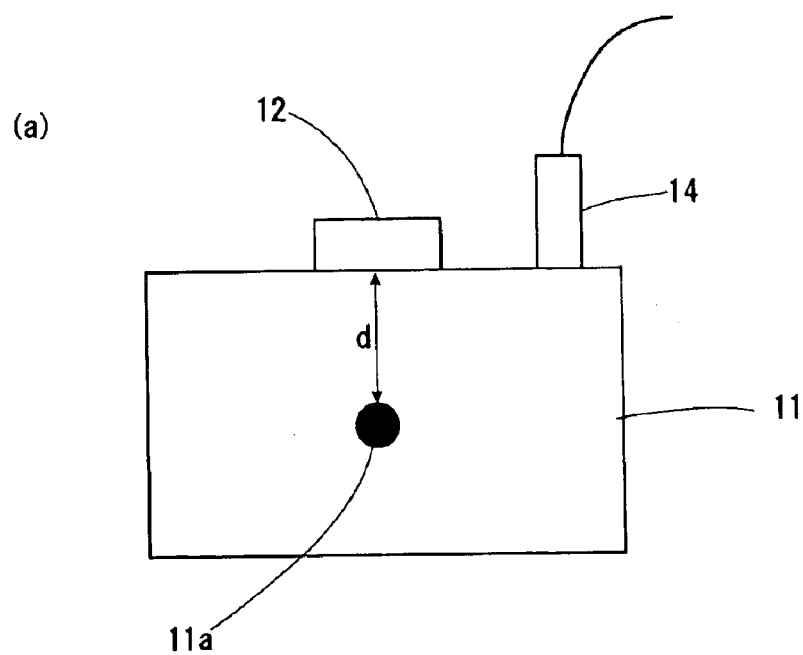
(a)
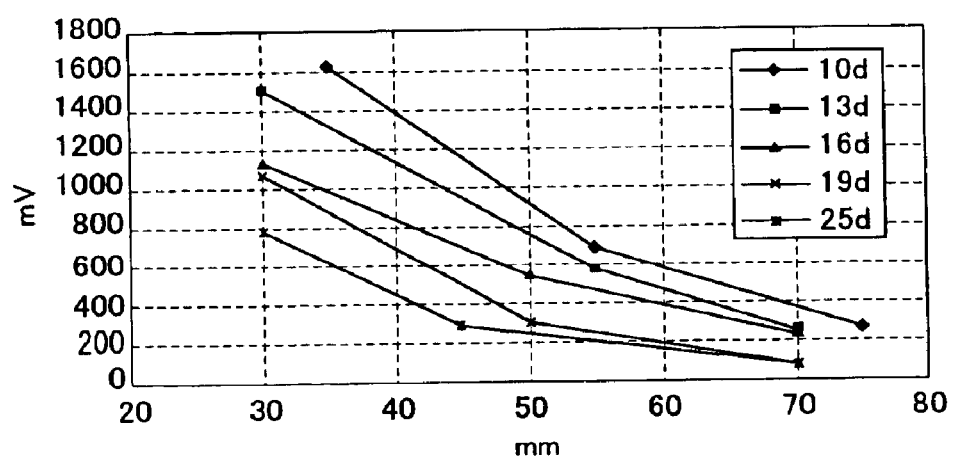
(b)

F I G. 2 4
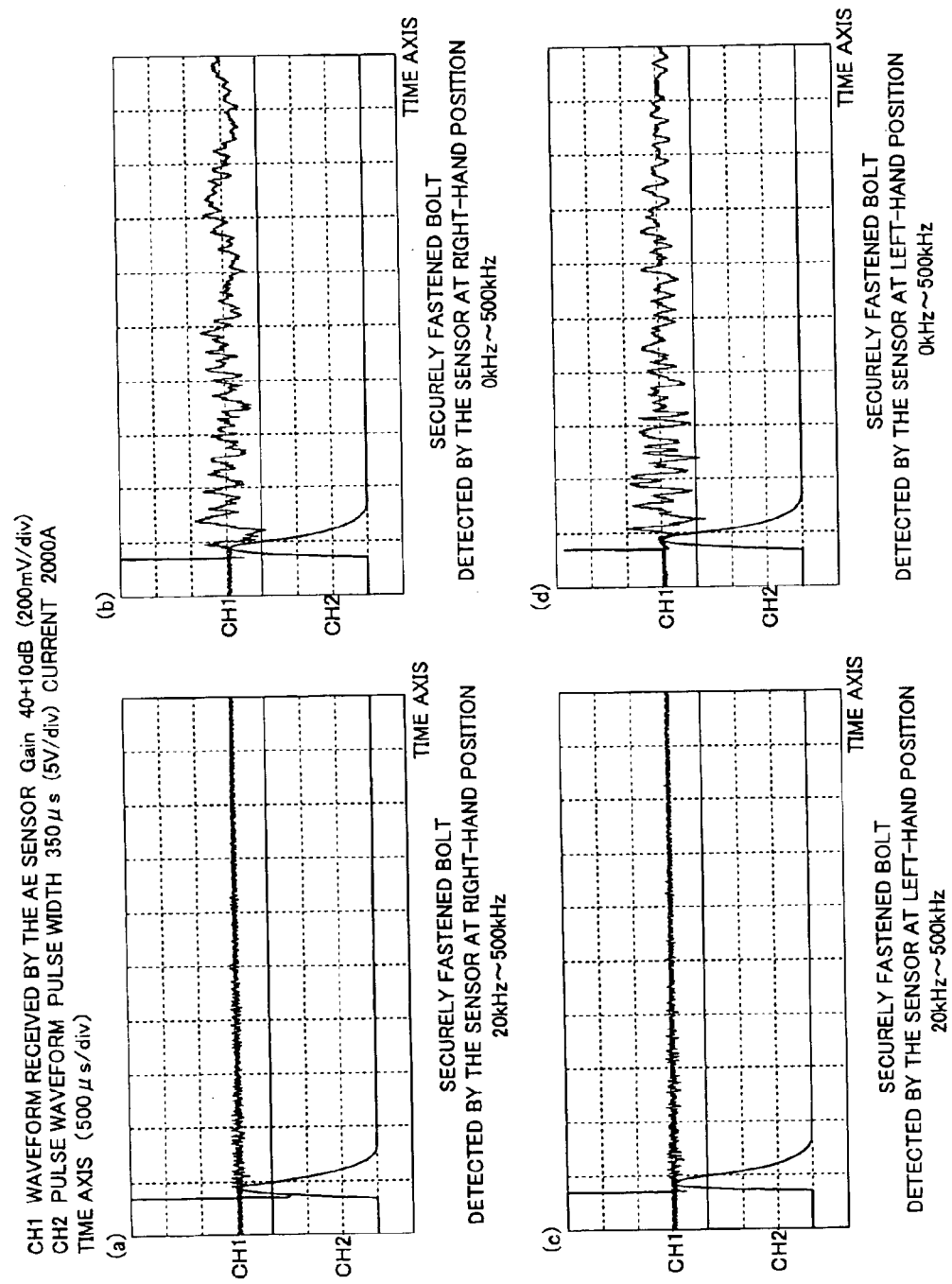

FIG. 27
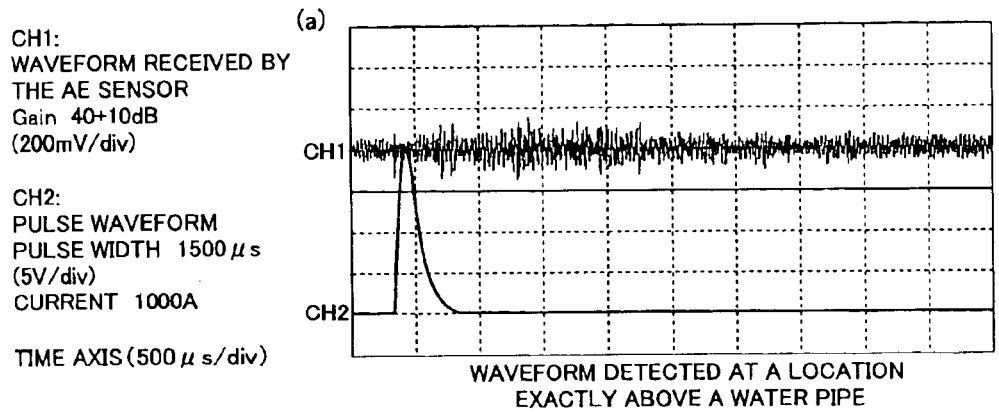
WAVEFORM DETECTED AT A LOCATION EXACTLY ABOVE A WATER PIPE
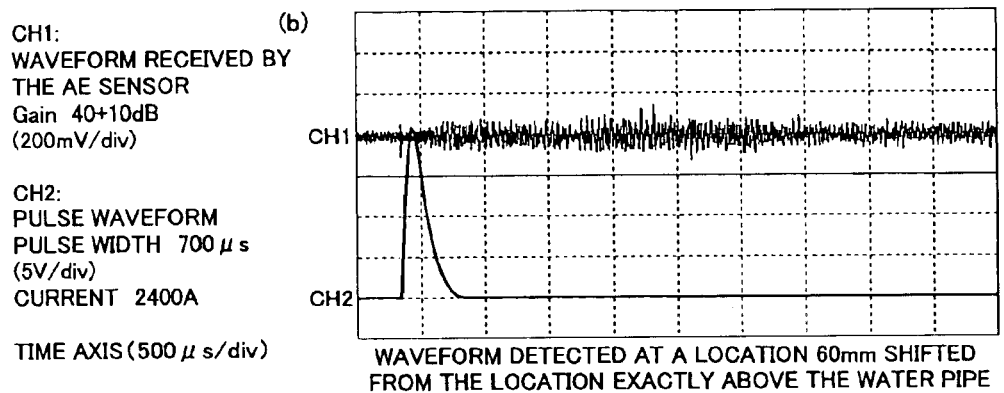
WAVEFORM DETECTED AT A LOCATION 60mm SHIFTED FROM THE LOCATION EXACTLY ABOVE THE WATER PIPE
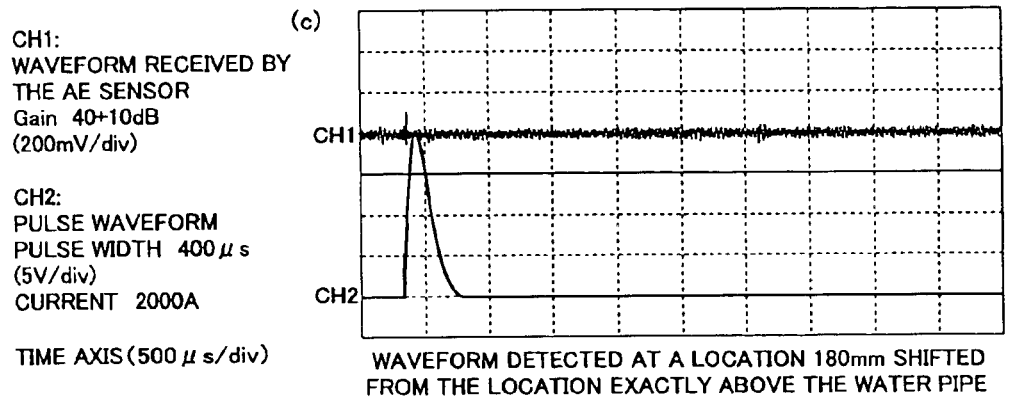
WAVEFORM DETECTED AT A LOCATION 180mm SHIFTED FROM THE LOCATION EXACTLY ABOVE THE WATER PIPE

DEVICE AND METHOD FOR ACOUSTIC DIAGNOSIS AND MEASUREMENT BY PULSE ELECTROMAGNETIC FORCE

TECHNICAL FIELD

The present invention relates to an acoustic diagnosis/measurement apparatus using a pulse of electromagnetic force for diagnosing/measuring a structure including a conductor and a non-conductive material covering the conductor, and a method of diagnosing/measuring such a structure, in particular, in terms of corrosion or adhesion of a reinforcing iron rod in reinforced concrete, the location of the reinforcing iron rod, the diameter of the reinforcing iron rod, presence/absence of a fracture in the reinforcing iron rod, or the location of the fracture, or in terms of the location of a water pipe buried in the ground, or in terms of whether a conductor is securely bound by a binding member.

BACKGROUND ART

In a structure made of reinforced concrete, such as a tunnel, a bridge, a building, a retaining wall, a dam, or a civil construction, in order to evaluate the strength or life or to determine construction procedure, it is needed to detect locations of reinforcing iron rods, diameters of reinforcing iron rods, the degree of corrosion of reinforcing iron rods, and/or adhesion strength of reinforcing iron rods, for the purpose of, for example, evaluation of strength or life of the structure or determination of procedure of construction. Various techniques for the above purpose are known. They include radiography for taking an X-ray image of a structure placed between an X-ray generator and a film, ultrasonic diagnosis in which an ultrasonic wave is generated by an ultrasonic generator placed on the surface of concrete and diagnosis/measurement is performed on the basis of detection of a reflected ultrasonic wave, a percussion method in which diagnosis/measurement is performed on the basis of an echo detected after tapping a surface of a structure with a hammer or the like, an infrared imaging method in which a surface of a structure is illuminated with an infrared ray, and a microwave method in which a surface of a structure is illuminated with a microwave.

However, the conventional methods of detecting locations of reinforcing iron rods or corrosion of reinforcing iron rods have problems as described below. For example, in radiography, it is needed to put a structure between the X-ray generator and the film, and thus this method has various limitations such as those on the shape, the size, and the location. This method cannot be substantially used for tunnels, dams, or the like. Another problem is that control is needed so as to prevent a human body from being significantly damaged by an X-ray and thus it is not easy to employ this method.

In the detection of the locations of reinforcing iron rods using the percussion method, a high skill is needed. Because detection is based on the skill, it is difficult to achieve high reliability in detection. When diagnosis of corrosion is performed using this method, corrosion cannot be easily detected unless reinforcing iron rods are so significantly corroded that a void is created. In this method, detection of corrosion is based on the skill and thus the reliability of detection is low. For this reason, it is needed to partially expose a reinforcing iron rod and visually observe an exposed part to confirm.

In the ultrasonic diagnosis method, an ultrasonic wave is applied to the surface of reinforced concrete, and the location of a reinforcing iron rod is determined from an ultrasonic wave reflected from the reinforcing iron rod. However, the concrete includes gravel and a large number of non-continuous parts created by bubbles or the like, which cause the ultrasonic wave to be attenuated or scattered and thus make it difficult to perform analysis.

In the infrared imaging method and also in the microwave method, because the infrared ray or the microwave is greatly attenuated by concrete, measurement is possible only in a region near the surface of a structure.

As a for a method of diagnosing corrosion, it is known to detect an acoustic wave generated by elastic energy released when a structure is deformed or cracked and analyze the detected acoustic wave to determine the degree of corrosion of the structure. This method is known as an acoustic diagnosis method. More specifically, an acoustic emission (AE) sensor is attached to a structure and the output of the AE sensor is monitored over a long period of time to detect an acoustic emission which occurs accidentally and suddenly due to stress corrosion cracking. However, it is needed to continuously perform measurement over a long period and it is also needed to apply an unnecessarily large load. Thus, this technique is not suitable for detection of corrosion of a structure.

As described above, no conventional method is known which allows high-reliability non-destructive detection of the degree of corrosion of reinforcing iron rods in reinforced concrete, adhesion strength between concrete and reinforcing iron rods, or the location or the diameter of a reinforcing iron rod in concrete. The lack of effective methods causes an error to occur in prediction of strength or life, and thus can cause an unpredictable disaster to occur.

In structures including a prestressed conductor and a non-conductive material covering the conductor, that is, structures made of prestressed-concrete, such as bridges, electric poles, and railroad ties, reinforcing iron rods prestressed so as to enhance their elasticity are embedded in concrete. When such a structure is used for a long period, there is a possibility that a reinforcing iron rod fractures. However, no conventional technique is known which allows such a fracture to be detected in a non-destructive fashion. Therefore, periodical replacement at scheduled intervals is needed, or otherwise an unpredictable disaster can occur.

In a civil engineering work or a construction work in which it is required to drive stakes into ground, it is necessary to know the locations of existing water pipes or gas pipes buried in the ground. In this case, water pipes and gas pipes are conductors embedded in a non-conductive material. Conventionally, a metal detector or sonar is used to determine the buried location. However, such an apparatus is complicated and special technical knowledge is needed to handle it. There is no technique which can be easily used to detect a precise location under ground. Thus, in many cases, a troublesome job, such as digging up the ground, is needed to make confirmation.

In the case of a structure including a plurality of conductors bound with each other via a binding member, such as a bridge constructed as a road by joining iron plates using bolts and nuts, for the purpose of safety, it is necessary to periodically examine whether bolts and nuts are maintained in a securely fastened state. However, in structures having a large size such as bridges, large bolts and nuts are used and they are fastened by very large torque. Therefore, it is impossible to manually diagnose using a torque wrench or the like, and diagnosis is performed using a dedicated machine having a large size. Another problem in such diagnosis is that it is necessary to close the bridge during the diagnosis.

In view of the above, a first object of the present invention is to provide an apparatus for diagnosing or measuring, non-destructively and precisely, a structure including a conductor and a non-conductive material covering the conductor in terms of the degree of corrosion, the adhesive strength, the cover depth, and the diameter of the conductor. A specific example is an apparatus for non-destructively diagnosing or measuring the degree of corrosion of reinforcing iron rods in reinforced concrete, the strength of adhesion between reinforcing iron rods and concrete, and/or the cover depth or the diameter of reinforcing iron rods in concrete.

A second object of the present invention is to provide an apparatus for non-destructively and precisely measuring the location of a concoctor in a structure including the conductor and a non-conductive material covering the conductor. A specific example is an apparatus for non-destructively and precisely measuring the location of reinforcing iron rods in reinforced concrete.

A third object of the present invention is to provide an apparatus for diagnosing or measuring, in detail, the degree of corrosion, the adhesion strength, and/or the location of a conductor in a structure including the conductor and a non-conductive material covering the conductor, on the basis of a distribution of small vibrations over the entire surface and a propagation mode of vibrations. A specific example is an apparatus for non-destructively diagnosing or measuring the degree of corrosion of reinforcing iron rods in reinforced concrete, the strength of adhesion between reinforcing iron rods and concrete, and/or the location of reinforcing iron rods in concrete.

A fourth object of the present invention is to provide a method of non-destructively and precisely diagnosing or measuring the degree of corrosion and/or the adhesion strength of a conductor in a structure including the conductor and a non-conductive material covering the conductor. A specific example is a method of non-destructively diagnosing or measuring the degree of corrosion of reinforcing iron rods in reinforced concrete and/or the strength of adhesion between reinforcing iron rods and concrete.

A firth object of the present invention is to provide a method of non-destructively and precisely measuring the location of a conductor in a structure including the conductor and a non-conductive material covering the conductor. A specific example is a method of non-destructively measuring the location of reinforcing iron rods in reinforced concrete.

A sixth object of the present invention is to provide a method of non-destructively and precisely measuring the location of a conductor in a structure including the conductor and a non-conductive material covering the conductor. A specific example is a method of non-destructively diagnosing or measuring, in detail, the degree of corrosion of reinforcing iron rods in reinforced concrete, the strength of adhesion between reinforcing iron rods and concrete, and/or the location of reinforcing iron rods in concrete, on the basis of a distribution of small vibrations over the entire surface and a propagation mode of vibrations.

A seventh object of the present invention is to provide a method of measuring the diameter or the cover depth of a conductor in a structure including the conductor and a non-conductive material covering the conductor. A specific example is a method of measuring the diameter or the cover depth of reinforcing iron rods in reinforced concrete.

An eighth object of the present invention is to provide a method of diagnosing or measuring whether conductors bound with each other via a binding member are in a state in which the conductors are securely bound by the binding member. A specific example is a method of diagnosing or measuring whether iron plates bound with each other via a bolt and a nut are in a state in which the iron plates are securely bound by the bolt and the nut.

A ninth object of the present invention is to provide a method of non-destructively and precisely diagnosing or measuring the location of a conductor embedded in a non-conductive material. A specific example is a method of diagnosing or measuring the location of a water pipe or a gas pipe buried under the ground.

A tenth object of the present invention is to provide a method of non-destructively and precisely diagnosing or measuring a structure including a conductor and a non-conductive material covering the conductor as to whether the conductor has a fracture. A specific example is a method of determining whether a bridge, an electric pole, or a railroad tie, which are made of prestressed concrete, has a fracture and/or measuring the location of such a fracture.

DISCLOSURE OF THE INVENTION

To achieve the above objects, the present invention provides an acoustic diagnosis/measurement apparatus using a pulse of electromagnetic force, comprising a coil attached to a surface of a structure including a conductor and a non-conductive material covering the conductor; a power supply unit for supplying a current pulse to the coil; an acoustic transducer attached to the surface of the structure or to a part of the conductor, the part being separated from the non-conductive material; and a measurement unit for measuring an output waveform of the acoustic transducer, whereby corrosion of the conductor, adhesion strength of the conductor, the cover depth of the conductor, and/or the diameter of the conductor are diagnosed or measured.

In this apparatus, when the structure subjected to the measurement is, for example, reinforced concrete, an acoustic wave is generated from an acoustic wave source at the location of the reinforcing iron rod directly excited by the magnetic field pulse and the acoustic wave propagates through the structure to the surface thereof. The acoustic wave propagating to the surface of the structure varies depending on the degree of corrosion and/or adhesion of the reinforcing iron rod. Therefore, by analyzing the acoustic waveform, it is possible to diagnose or measure the degree of corrosion and the adhesion strength. The amplitude of the acoustic waveform also varies depending on the diameter of the reinforcing iron rod and the cover depth of the reinforcing iron rod. If the depth of the reinforcing iron rod is known, the diameter of the reinforcing iron rod can be determined. Conversely, if the diameter of the reinforcing iron rod is known, the cover depth can be determined.

In this technique, because the reinforcing iron rod is directly excited by the magnetic field pulse, a very large acoustic waveform can be obtained compared with that obtained in the conventional technique in which an ultrasonic wave generated by an ultrasonic source is reflected from the reinforcing iron rod. Furthermore, in this technique according to the present invention, unlike the conventional percussion method, the degree of corrosion, the strength of adhesion, the cover depth, and/or the diameter of the reinforcing iron rod can be diagnosed or measured non-destructively in a highly reliable fashion.

The present invention also provides an acoustic diagnosis/measurement apparatus using a pulse of electromagnetic force, comprising a coil attached to a surface of a structure including a conductor and a non-conductive material covering the conductor; a power supply unit for supplying a current pulse to the coil; a plurality of acoustic transducers attached at different locations on the surface of the structure; and a measurement unit for measuring acoustic propagation delays from outputs of the acoustic transducers, whereby the location of the conductor is measured.

In this apparatus, an acoustic wave is generated from an acoustic wave source at the location of the reinforcing iron rod directly excited by the magnetic field pulse and the acoustic wave propagates through the structure to the surface thereof. On the basis of propagation delay times of the acoustic wave measured at different locations, the location of the reinforcing iron rod can be precisely determined non-destructively.

The present invention provides an acoustic diagnosis/measurement apparatus using a pulse of electromagnetic force, comprising a coil attached to a surface of a structure including a conductor and a non-conductive material covering the conductor; a power supply unit for supplying a current pulse to the coil; and a displacement detector for optically measuring displacement of the surface of the structure thereby measuring a vibration of the surface of the structure; whereby the location of the conductor, corrosion of the conductor, and/or adhesion strength of the conductor are diagnosed or measured.

In this apparatus, an acoustic wave is generated from an acoustic wave source at the location of the reinforcing iron rod directly excited by the magnetic field pulse and the acoustic wave propagates through the structure to the surface thereof. By employing a laser interferometer as the displacement detector, it is possible to detect the distribution of small vibrations over the entire surface and it is also possible to detect the propagation mode of vibrations, and thus it is possible to obtain further detailed information in a non-destructive fashion.

Preferably, the acoustic transducer is an element for converting an acoustic signal into an electric signal, selected from a group consisting of an acoustic emission sensor, an acceleration sensor, and a microphone.

The displacement detector may be a laser interferometer for illuminating a surface of the structure with a coherent laser beam and detecting a phase difference as an interference pattern of a reflected laser beam, the phase difference varying depending on a vibration of a surface of the structure.

The coil may be a single coil or may include a plurality of subcoils. In the case in which a plurality of subcoils are used, the plurality of subcoils are disposed coaxially such that adjacent coils are in close contact with each other. The power supply unit may include charge storage capacitors connected in series to the respective subcoils and a power source connected, via a common switch and in parallel, to each series connection of one subcoil and one capacitor, whereby a current pulse is applied to subcoils by turning on the common switch thereby generating a magnetic field pulse.

When the coil is formed using a plurality of subcoils, the inductance of each of subcoils forming the coil is smaller than is in the case in which the coils is formed of a single coil, and the capacitor of each charge storage capacitor can be reduced. This makes it possible to reduce the time constant of a current pulse which flows through each subcoil in response to turning on the common switch. The magnetic field pulses generated by the subcoils are superimposed, and thus it is possible to generate an overall magnetic field pulse having a large crest value and a small pulse width. The capability of generating a magnetic field pulse with a large crest value and a small pulse width makes it possible to strongly excite a reinforcing iron rod, which allows diagnosis/measurement to be performed non-destructively in a high reliable fashion.

It is desirable to add a magnet for generating a static magnetic field to the coil.

This makes it possible to further strongly excite the reinforcing iron rod and thus it makes possible to perform diagnosis/measurement of a reinforcing iron rod located at deeper depth with respect to the surface of the structure.

The measurement unit for measuring the output waveform may measure the output waveform in the time domain, display the measured output waveform, extract a feature associated with corrosion and/or adhesion from the waveform in the time domain, and display the extracted feature, or may calculate a waveform in the frequency domain, that is, a frequency spectrum, by performing a Fourier transform on the original output waveform, display the calculated waveform in the frequency domain, extract a feature associated with corrosion and/or adhesion from the waveform in the frequency domain, and display information associated with the corrosion and/or adhesion.

This measurement unit is capable of instantly performing diagnosis/measurement of corrosion and/or corrosion from the waveform in the time domain or frequency domain.

The feature extracted from the waveform in the time domain may be a pattern, a shape factor, or a crest factor of the waveform in the time domain, and the displaying of information associated with the corrosion and/or adhesion may include comparing the form factor or the crest factor with a predetermined threshold value and displaying whether or not there is a problem in terms of the corrosion and/or the adhesion.

The shape factor and the crest factor vary sensitively depending on corrosion and/or adhesion, and thus it is possible to easily detect corrosion and/or adhesion from the shape factor and the crest factor. The measured shape factor or crest factor is compared with a predetermined threshold value, and information whether there is a problem in terms of corrosion/adhesion is displayed. Thus, any user can correctly perform diagnosis/measurement without having to have a high skill.

The feature extracted from the waveform in the time domain may be a similarity factor extracted from the shape of the envelope curve of the waveform in the time domain, and the displaying of information associated with the corrosion and/or adhesion may include comparing the similarity factor with a predetermined threshold value and displaying whether or not there is a problem in terms of the corrosion and/or the adhesion.

Aging effects are reflected in the similarity factor, and thus high-reliability diagnosis/measurement can be performed on the base of the similarity factor. The measured similarity factor is compared with a predetermined threshold value, and information whether there is a problem in terms of corrosion/adhesion is displayed. Thus, any user can correctly perform diagnosis/measurement without having to have a high skill.

The feature extracted from the waveform in the time domain may be a normalized waveform obtained by dividing each value of the waveform in the time domain by the effective value of the waveform in the time domain or a waveform obtained by exponentiation of the normalized waveform.

If the waveform in the time domain is normalized by dividing each value of the waveform in the time domain by the effective value of the waveform in the time domain, the feature of the original waveform becomes clearer. The feature of the original waveform becomes further clearer by exponentiation. Thus, it becomes possible to perform high-sensitive diagnosis/measurement.

The similarity factor may be extracted from the envelope curve of the normalized waveform and compared with a predetermined threshold value. Depending on the comparison result, information indicating whether or not there is a problem in terms of the corrosion and/or the adhesion may be displayed.

Because the similarity factor is determined from the normalized waveform, it becomes possible for any user to easily perform correct diagnosis/measurement in a further sensitive fashion.

The feature extracted from the waveform in the frequency domain may be a waveform pattern in the frequency domain, and the displaying of information associated with the corrosion and/or adhesion may include comparing the waveform pattern with a predetermined pattern, and displaying whether or not there is a problem in terms of the corrosion and/or the adhesion.

In the vibration of a reinforcing iron rod excited by a pulse of electromagnetic force, the degree of freedom of vibration varies depending on corrosion/adhesion of the reinforcing iron rod, and thus the degree of corrosion/adhesion is very sensitively reflected in the frequency spectrum. Because information is displayed which indicates whether or not there is a problem in terms of corrosion/adhesion determined based on the comparison of the frequency spectrum with a predetermined reference frequency pattern, any user can easily perform correct diagnosis/measurement without having to have a high skill.

The feature extracted from the waveform in the frequency domain may be a normalized waveform obtained by dividing each value of the waveform in the frequency domain by the effective value of the waveform in the time domain or a waveform obtained by the exponentiation of the normalized waveform, and the displaying of information associated with the corrosion and/or adhesion may include extracting the similarity factor from the envelope curve of the normalized waveform, comparing the similarity factor with a predetermined threshold value, and displaying whether or not there is a problem in terms of the corrosion and/or the adhesion.

The waveform in the frequency domain is very sensitive to the degree of corrosion and/or adhesion strength. If this waveform in the frequency domain is normalized by dividing each value of the waveform in the frequency domain by the effective value, the feature of the original waveform is emphasized in the resultant normalized waveform. Thus, highly sensitive diagnosis/measure of corrosion/adhesion is possible. Furthermore, if the similarity factor is determined from the normalized waveform, high-sensitive and high-reliability diagnosis/measurement is possible. The measured similarity factor is compared with a predetermined threshold value, and information whether there is a problem in terms of corrosion/adhesion is displayed. Thus, any user can correctly perform diagnosis/measurement without having to have a high skill.

The displacement detector may be a laser interferometer for illuminating a surface of the structure with a coherent laser beam and detecting a phase difference as an interference pattern of a reflected laser beam, the phase difference varying depending on a vibration of a surface of the structure.

The present invention also provides a method of acoustic diagnosis/measurement using a pulse of electromagnetic force, comprising the steps of attaching a coil to a surface of a structure including a conductor and a non-conductive material covering the conductor; applying a current pulse to the coil thereby generating a magnetic field pulse; inducing an eddy current in the conductor by the magnetic field pulse; oscillating the conductor by interaction between the eddy current and the magnetic field pulse thereby generating an acoustic wave; converting an acoustic signal of the acoustic wave into an electric signal by using an acoustic transducer attached to the surface of the structure or attached to a part of the conductor, the part of the conductor being separated from the non-conductive material; and measuring the waveform of the electric signal to perform diagnosis and/or measurement in terms of corrosion and/or adhesion of the conductor.

In this method, when the structure subjected to the measurement is, for example, reinforced concrete, an acoustic wave is generated from an acoustic wave source at the location of the reinforcing iron rod directly excited by the magnetic field pulse and the acoustic wave propagates through the structure to the surface thereof. The acoustic wave propagating to the surface of the structure varies depending on the degree of corrosion and/or adhesion of the reinforcing iron rod. Therefore, by analyzing the acoustic waveform, it is possible to diagnosing or measuring the degree of corrosion and the adhesion strength.

In this technique, because the reinforcing iron rod is directly oscillated by the magnetic field pulse, a very large acoustic waveform can be obtained compared with that obtained in the conventional technique in which an ultrasonic wave generated by an ultrasonic source is reflected from the reinforcing iron rod. Thus, the degree of corrosion, the strength of adhesion, the cover depth, and/or the diameter of the reinforcing iron rod can be diagnosed or measured non-destructively.

The present invention also provides a method of acoustic diagnosis/measurement using a pulse of electromagnetic force, comprising the steps of attaching a coil to a surface of a structure including a conductor and a non-conductive material covering the conductor; applying a current pulse to the coil thereby generating a magnetic field pulse; inducing an eddy current in the conductor by the magnetic field pulse; oscillating the conductor by interaction between the eddy current and the magnetic field pulse thereby generating an acoustic wave; converting an acoustic signal of the acoustic wave into electric signals by using a plurality of acoustic transducers attached at different locations on the surface of the structure; and measuring propagation delay times of the acoustic wave corresponding to the respective electric signals; and measuring the location of the conductor on the basis of the propagation delay times.

In this method, an acoustic wave is generated from an acoustic wave source at the location of the reinforcing iron rod directly excited by the magnetic field pulse and the acoustic wave propagates through the structure to the surface thereof. On the basis of propagation delay times of the acoustic wave measured at different locations, the location of the reinforcing iron rod can be precisely determined non-destructively.

The present invention also provides a method of acoustic diagnosis/measurement using a pulse of electromagnetic force, comprising the steps of attaching a coil to a surface of a structure including a conductor and a non-conductive material covering the conductor; applying a current pulse to the coil thereby generating a magnetic field pulse; inducing an eddy current in the conductor by the magnetic field pulse;

oscillating the conductor by interaction between the eddy current and the magnetic field pulse thereby generating an acoustic wave; detecting an optical displacement corresponding to a surface vibration of the structure generated by the acoustic wave thereby diagnosing the location of the conductor and the state of the structure.

In this method, an acoustic wave is generated from an acoustic wave source at the location of the reinforcing iron rod directly excited by the magnetic field pulse and the acoustic wave propagates through the structure to the surface thereof. By employing a laser interferometer as the displacement detector, it is possible to detect the distribution of small vibrations over the entire surface and it is also possible to detect the propagation mode of vibrations, and thus it is possible to perform further detailed diagnosis in a non-destructive fashion.

The present invention also provides a method of acoustic diagnosis/measurement using a pulse of electromagnetic force, comprising the steps of disposing a coil on a surface of a non-conductive material covering a conductor; applying a current pulse to the coil thereby generating a magnetic field pulse; inducing an eddy current in the conductor by the magnetic field pulse; oscillating the conductor by interaction between the eddy current and the magnetic field pulse thereby generating an acoustic wave; converting an acoustic signal of the acoustic wave into an electric signal by using an acoustic transducer attached to the surface of the structure; and measuring the waveform of the electric signal to measure the diameter of the conductor or measure the cover depth of the conductor.

In this method, the amplitude of the acoustic waveform varies depending on the diameter of the reinforcing iron rod and the cover depth of the reinforcing iron rod. If the depth of the reinforcing iron rod is known, the diameter of the reinforcing iron rod can be determined. Conversely, if the diameter of the reinforcing iron rod is known, the cover depth can be determined.

The present invention also provides a method of acoustic diagnosis/measurement using a pulse of electromagnetic force, comprising the steps of disposing a coil at a location exactly above a connecting part of a plurality of conductors bound with each other via a binding member; applying a current pulse to the coil thereby generating a magnetic field pulse; inducing an eddy current in a conductor facing the coil by the magnetic field pulse; oscillating the conductor by interaction between the eddy current and the magnetic field pulse thereby generating an acoustic wave; converting an acoustic signal of the acoustic wave into an electric signal by using an acoustic transducer attached to the conductor facing the coil and by using an acoustic transducer attached to another conductor bound with the former conductor; and comparing the waveform of the electric signal output by the acoustic transducer attached to the conductor facing the coil with the waveform of the electric signal output by the acoustic transducer attached to the other conductor, thereby performing diagnosis and/or measurement as to whether the binding member is in a securely fastened state.

In this method, the magnitude of a vibration propagating into the conductor from the other conductor facing the coil varies depending on the fastening degree. Thus, the fastening degree can be diagnosed or measured. This method is useful in particular when a set of a bolt and a nut is used as the binding member.

The present invention also provides a method of acoustic diagnosis/measurement using a pulse of electromagnetic force, comprising the steps of disposing a coil on a surface of a non-conductive material covering a conductor; applying a current pulse to the coil thereby generating a magnetic field pulse; inducing an eddy current in the conductor by the magnetic field pulse; oscillating the conductor by interaction between the eddy current and the magnetic field pulse thereby generating an acoustic wave; converting an acoustic signal of the acoustic wave into an electric signal by using an acoustic transducer attached to a part of the conductor, the part of the conductor being separated from the non-conductive material; changing the location of the coil disposed on the surface of the non-conductive material; and measuring a change in the electric signal caused by the change in the location of the coil there by measuring the location of the conductor.

In this method, the conductor is oscillated most strongly when the coil comes to a location closest to the conductor. Thus, the location of the conductor can be diagnosed or measured. This method is useful in particular when the conductor is an underground water pipe or gas pipe.

The present invention also provides a method of acoustic diagnosis/measurement using a pulse of electromagnetic force, comprising the steps of attaching a coil to a surface of a structure including a conductor and a non-conductive material covering the conductor; applying a current pulse to the coil thereby generating a magnetic field pulse; inducing an eddy current in the conductor by the magnetic field pulse; oscillating the conductor by interaction between the eddy current and the magnetic field pulse thereby generating an acoustic wave; converting an acoustic signal of the acoustic wave into an electric signal by using an acoustic transducer attached to a part of the conductor, the part of the conductor being separated from the non-conductive material; and diagnosing whether the conductor has a fracture, on the basis of the strength of the electric signal and, if necessary, diagnosing the location of the fracture of the conductor by changing the location of the coil disposed on the surface of the structure and measuring a change in the electric signal caused by the change in the location of the coil.

In this method, an acoustic signal propagating through a reinforcing iron rod is attenuated by a fracture, and thus it is possible to detect whether or not there is a fracture. Furthermore, if a change in attenuation is measured while changing the location of the coil disposed on the surface of a structure, it is possible to detect the location of the fracture. This method is useful in particular when the structure is made of prestressed concrete, such as a bridge, an electric pole, or a railroad tie made of prestressed concrete.

Thus, according to the present invention, it is possible to non-destructively and precisely diagnose/measure not only the location of an reinforcing iron rod in concrete but also corrosion, adhesion strength, and/or rust of the reinforcing iron rod and further a separation or a crack of concrete in diagnosis/measurement of a structure made of reinforced concrete, such as a tunnel, a bridge, a building, a retaining wall, a dam, or a civil construction. This makes it possible to prevent a structure made of reinforced concrete from breaking down or prevent a piece of concrete from separating from the main part. Thus it becomes possible to precisely predict the remaining life of a structure made of reinforced concrete and perform maintenance/management of the structure made of reinforced concrete in a highly reliable fashion.

The cover depth and/or the diameter of a reinforcing iron rod can also be measured.

It is also possible to easily determine whether a binding member such as a set of a bolt and a nut is securely fastened.

It is also possible to easily determine the location of a water pipe or a gas pipe buried in the ground.

It is also possible to diagnose whether a reinforcing iron rod has a fracture.

BRIEF DESCRIPTION OF THE DRAWINGS

The present invention will become more apparent from the following detailed description of the preferred embodiments with reference to the accompanying drawings. Note that the embodiments described with reference to the accompanying drawing are presented for the purpose of illustration and ease of understanding of the invention and are not intended to limit the invention.

FIGS. 1(a) and 1(b) are conceptual diagrams showing the embodiment of the acoustic diagnosis/measurement apparatus using a pulse of electromagnetic force according to claim 1 of the present invention and the method therefor, FIG. 1(a) shows a manner in which an acoustic transducer is attached to a surface of concrete, FIG. 1(b) shows a manner in which the acoustic transducer is attached to an exposed part of an iron rod.

FIGS. 2(a) and 2(b) are diagrams showing the shape of a test sample of reinforced concrete used herein in the first example and also showing a measurement system, wherein FIG. 2(a) is a plan view and FIG. 2(b) is a side view thereof.

FIGS. 3(a) and 3(b) are diagrams showing measured acoustic waveforms, wherein an acoustic waveform observed for the normal block is shown in FIG. 3(a) and an acoustic waveform observed for the cracked block is shown in FIG. 3(b).

FIG. 4 is a schematic diagram showing an acoustic diagnosis/measurement apparatus using a pulse of electromagnetic force according to the present invention.

FIG. 5(a) to 5(c) show the surface shape of reinforced concrete used in an embodiment and a method of producing the reinforced concrete, wherein FIG. 5(a) shows the surface shape of the reinforced concrete, FIG. 5(b) shows an outer frame used to produce the reinforced concrete, and FIG. 5(c) shows the external appearance of produced reinforced concrete.

FIG. 6 is a diagram showing propagation delay times in the reinforced concrete, measured at different distances from the acoustic wave source.

FIGS. 9(a) and 9(b) show an example of the waveform of a current pulse applied to a coil from a power source and an example of a measured acoustic signal generated thereby, wherein the example shown in FIG. 9(a) is according to a conventional technique, and the example shown in FIG. 9(b) is according to the present invention.

FIG. 12 is a table showing the shape factors SF and the crest factors CF for the respective test blocks (A), (B), and (C).

FIG. 13(a) shows the envelope curves determined for the respective test blocks (A), (B), and (C), and FIG. 13(b) shows the corresponding logarithmic inverse envelope curves.

FIGS. 14(a), 14(b), and 14(c) respectively show the time-domain waveform, the normalized waveform, and the square of the normalized waveform, obtained for the test block (A).

FIGS. 15(a) and 14(b) respectively show the cube and the quartic of the normalized waveform of the test block (A).

FIGS. 16(a), 16(b), and 16(c) respectively show the time-domain waveform, the normalized waveform, and the square of the normalized waveform, obtained for the test block (B).

FIGS. 17(a) and 17(b) respectively show the cube and the quartic of the normalized waveform of the test block (B).

FIGS. 18(a), 18(b), and 18(c) respectively show the time-domain waveform, the normalized waveform, and the square of the normalized waveform, obtained for the test block (C).

FIGS. 19(a) and 19(b) respectively show the cube and the quartic of the normalized waveform of the test block (C).

FIG. 22(a) is a diagram showing a method of measuring the diameter or the cover depth of a reinforcing iron rod according to the present invention, and FIG. 22(b) is a graph showing a measurement result.

FIGS. 23(a) and 23(b) are diagrams showing a method of diagnosing or measuring the secureness of a binding member, according to the present invention, wherein FIG. 23(a) is a side view of a conductor 21 and a conductor 22 bound together via a bolt 22 and a nut 23, and FIG. 23(b) is a plan view thereof.

FIGS. 24(a) to 24(d) are diagrams showing a measurement result obtained when the bolt and the nut are securely fastened, wherein FIGS. 24(a) and 24(b) show output waveforms of an acoustic transducer 14R attached to the conductor 21 located closer to a coil, and FIGS. 24(c) and 24(d) show output waveforms of an acoustic transducer 14L attached to the conductor 22 bound with the conductor 21 by the bolt and the nut.

FIGS. 25(a) to 25(d) are diagrams showing a measurement result obtained when the bolt and the nut are in a loosely coupled state, wherein FIGS. 25(a) and 25(b) show output waveforms of the acoustic transducer 14R attached to the conductor 21 located closer to a coil, and FIGS. 25(c) and 25(d) show output waveforms of the acoustic transducer 14L attached to the conductor 22 bound with the conductor 21 by the bolt and the nut.

FIGS. 26(a) and 26(b) are diagrams showing a method of measuring the location of a conductor embedded in a non-conductive material, wherein FIG. 26(a) is a side view showing a manner in which an acoustic transducer 14 is attached to an exposed part 33 of a water pipe 32 buried in the ground 31 which is non-conductive, and a coil 12 is disposed on the surface 34 of ground 31, and FIG. 26(b) is a plan view thereof.

FIGS. 27(a) to 27(c) are graphs showing results of measurement of the location of a water pipe buried in the ground, wherein FIG. 27(a) shows the waveform of an acoustic signal detected by the coil disposed exactly above the water pipe, FIG. 27(b) shows a waveform detected by the coil disposed on the ground at a location 60 mm apart from the location exactly above the water pipe, FIG. 27(c) shows a waveform detected by the coil disposed on the ground at a location 180 mm apart from the location exactly above the water pipe.

BEST MODE FOR CARRYING OUT THE INVENTION

Figure 2:
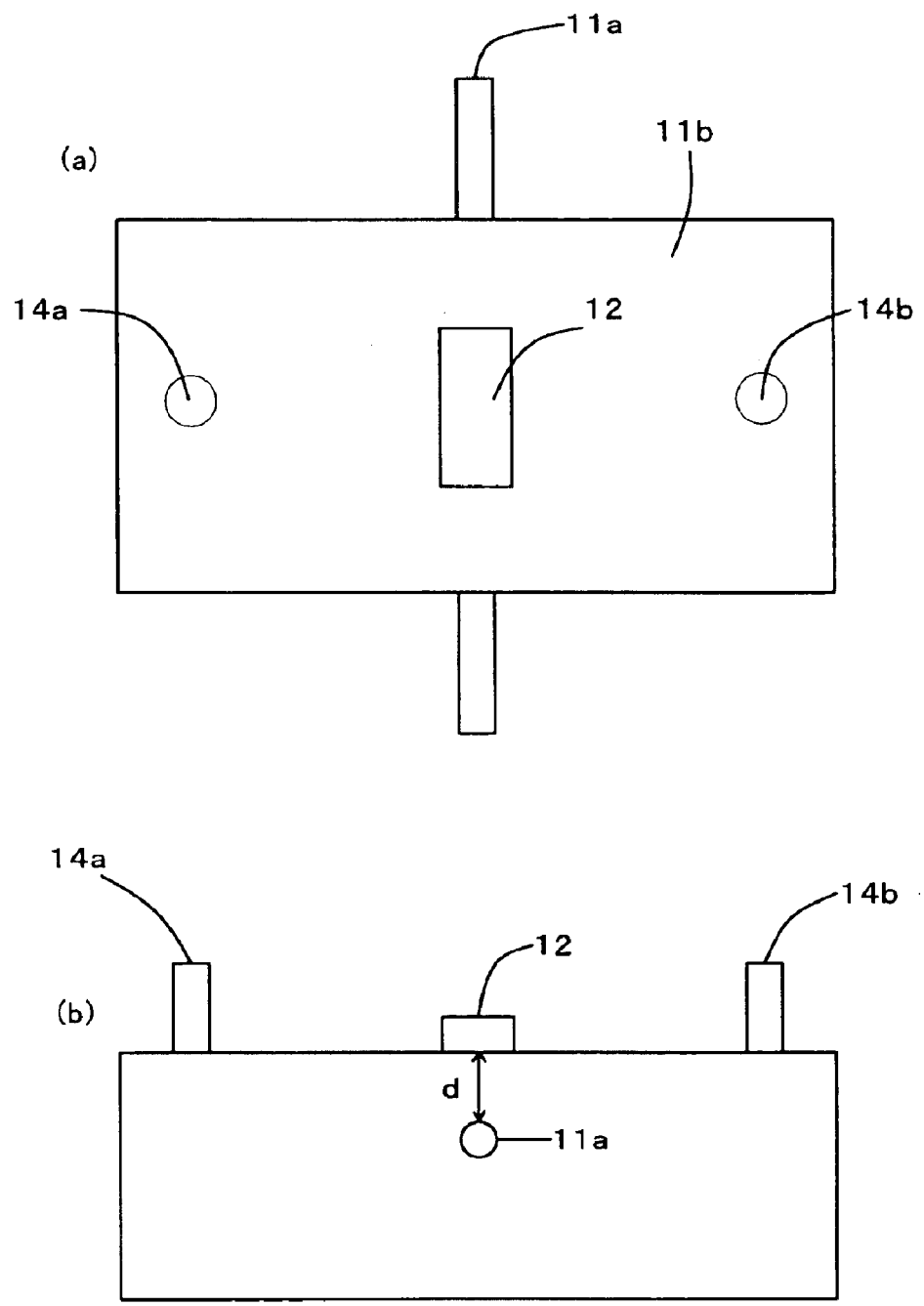

Embodiments of the present invention are described in detail below with reference to drawings.

First, an embodiment of an acoustic diagnosis/measurement apparatus using a pulse of electromagnetic force according to the present invention and a method therefor are described.

Herein, by way of example, the structure including a conductor and a non-conductive material covering the conductor subjected to diagnosis/measurement is assumed to be a structure made of concrete reinforced with iron rods.

The apparatus of the present embodiment is capable of making diagnosis/measurement in terms of corrosion, adhesion, cover depth, and diameters of iron rods.

FIGS. 1(a) and 1(b) are conceptual diagrams showing the embodiment of the acoustic diagnosis/measurement apparatus using a pulse of electromagnetic force according to the present invention and the method therefor, wherein FIG. 1(a) shows a manner in which an acoustic transducer is attached to a surface of concrete, and FIG. 1(b) shows a manner in which the acoustic transducer is attached to an exposed part of an iron rod.

In FIG. 1(a), the acoustic diagnosis/measurement apparatus using a pulse of electromagnetic force 10 includes a coil of an electric wire 12 attached to a surface of a reinforced concrete block 11 which is a structure to be examined, a power supply unit 13 for applying a current pulse to the coil 12, an acoustic transducer 14 attached to the surface of the reinforced concrete block 11, and a measurement unit 15 connected to the acoustic transducer 14 via a signal cable 17.

The coil 12 includes four coils each formed of 7 turns of a conductive wire with a diameter of, for example, 1.6 mm wound around a rectangular-shaped frame with a size of 50 mm×30 mm wherein those four coils are disposed coaxially and closely. The coil 12 is attached to the surface of the reinforced concrete block 11 to be examined. The power supply unit 13 is designed to apply a current pulse to the coil 12 via a power cable 16. The power supply unit 13 may be constructed in various manners depending on the size of the reinforced concrete block 11 and the location of the reinforcing iron rod 11a so that a desirable driving pulse is applied.

As for the acoustic transducer 14, a known acoustic transducer may be employed to detect a weak vibration and convert the detected vibration into an electric signal. The resultant electric signal is supplied to the measurement unit 15 via the signal cable 17.

As for the measurement unit 15, for example, a commercially available apparatus known as acoustic analyzer may be employed. The signal detected by the acoustic transducer 14 is amplified by an amplifier, and unnecessary components of the signal are removed by using a filter or the like. Acoustic analysis is then performed on the basis of the resultant signal. Another apparatus may also be used as the measurement unit 15. For example, in a case in which it is needed to measure only the waveform of the signal detected by the acoustic transducer 14, an oscilloscope or similar equipment may be employed.

In the acoustic diagnosis apparatus using a pulse of electromagnetic force 10 constructed in the above-described manner according to the present invention, if a current pulse is applied to the coil 12, a magnetic field pulse is generated toward the inside of the reinforced concrete 11, and the magnetic field pulse induces an eddy current in the reinforcing iron rod 11a which is conductive. A magnetic field is generated by the eddy current and it interacts with the magnetic field of the magnetic field pulse. As a result, the reinforcing iron rod 11a is oscillated. Herein, if the conductor 11a is made of a magnetic material, reinforcing iron rod 11a is further oscillated by a force associated with magnetic energy.

If the reinforcing iron rod 11a is oscillated, an acoustic wave is generated from the reinforcing iron rod 11a. The generated acoustic wave propagates to the surface and is detected by the acoustic transducer 14. The detected acoustic signal is converted into an electrical signal by the acoustic transducer 14 and supplied to the measurement unit 15 via the signal cable 17. The measurement unit 15 analyzes the waveform of the received electric signal to determine the degree of corrosion of the reinforcing iron rod 11a or determine whether the concrete 11b has a crack. If the reinforcing iron rod 11a has corroded, the acoustic wave generated by the reinforcing iron rod 11a is absorbed by a corroded portion, and attenuation of the acoustic wave occurs, which results in a reduction in the amplitude of the waveform observed by the measurement unit 15. Also in a case in which adhesion between the reinforcing iron rod and the concrete is weak, the amplitude of the waveform detected by the measurement unit 15 becomes small. A crack in the concrete results in attenuation of the acoustic wave, and thus the amplitude of the waveform detected by the measurement unit 15 becomes small. As described above, by comparing the amplitude of the acoustic wave, it is possible to detect the degree of damage of the reinforced concrete 11.

As shown in FIG. 1(b), it is also possible to detect corrosion or adhesion of a reinforcing iron rod by attaching the acoustic transducer 14 to an exposed portion of the reinforcing iron rod and directly detecting a vibration of the reinforcing iron rod.

Now, a first example is described.

In this first example, an example of measurement using the acoustic diagnosis/measurement apparatus using a pulse of electromagnetic force according to the present invention is described.

FIGS. 2(a) and 2(b) are diagrams showing the shape of a test sample of reinforced concrete used herein in the first example and also showing a measurement system, wherein FIG. 2(a) is a plan view and FIG. 2(b) is a side view thereof.

As shown in FIGS. 2(a) and 2(b), the test sample of reinforced concrete 11 includes rectangular-shaped concrete 11b with a size of 200 mm×150 mm×100 mm and a reinforcing iron rod 11a with a diameter of 13 mm embedded at a cover depth d of 30 mm measured from the upper surface of the concrete 11b and at a distance of 57 mm from the lower surface. The coil 12 is disposed on the surface of the reinforced concrete 11 at a location exactly above the reinforcing iron rod 11a. The acoustic transducers 14a and 14b are disposed on the surface of the reinforced concrete 11, at symmetrical locations opposing each other via the reinforcing iron rod 11a.

In the present example, a test sample of reinforced concrete with no crack in concrete 11b (normal test block) and a test sample of reinforced concrete with a crack extending in concrete 11b and reaching a reinforcing iron rod 11a (test block with crack) were prepared and they were excited under the same conditions. Acoustic waves were detected by the acoustic transducers 14a and 14b and the waveforms were compared.

The coil 12 used herein was formed by winding 25 turns an electric wire with a diameter of 1.0 mm around a core with a size of 30 mm×70 mm and had an internal resistance of 0.2 Ω. A current pulse with a crest value of 1000 A and a width of 1.5 ms was applied to the coil 12 thereby exciting the reinforcing iron rod 11a.

FIGS. 3(a) and 3(b) are diagrams showing measured acoustic waveforms, wherein an acoustic waveform observed for the normal block is shown in FIG. 3(a) and an acoustic waveform observed for the cracked block is shown in FIG. 3(b).

In FIGS. 3(a) and 3(b), CH1 and CH2 denote output waveforms of the acoustic transducers 14a and 14b, respectively, and CH3 denotes the waveform of the current pulse. The horizontal axis represents a time in units of 0.5 ms/div and the vertical axis represents the strength of the waveforms CH1 and CH2, wherein zero points of CH1 and CH2 are shifted from each other.

As can be seen from FIGS. 3(a) and 3(b), the crack significantly attenuates the acoustic wave generated by the reinforcing iron rod 11a excited by the current pulse.

Thus, it is possible to determine whether concrete has a crack.

Now, an embodiment of an acoustic diagnosis/measurement apparatus using a pulse of electromagnetic force according to the present invention and a corresponding method of acoustic diagnosis/measurement using a pulse of electromagnetic force are described below.

This apparatus is capable of measuring the location of a reinforcing iron rod in reinforced concrete.

FIG. 4 is a conceptual diagram showing an acoustic diagnosis/measurement apparatus using a pulse of electromagnetic force according to the present invention and a corresponding method.

As shown in FIG. 4, an acoustic location detector 20 includes a coil of an electric wire 12 attached to a surface of a reinforced concrete block 11, a power supply unit 13 (similar to that shown in FIG. 1, although not shown in FIG. 4) for applying a current pulse to the coil 12, a plurality of acoustic transducers 14 (14a, 14b, and 14c) attached to the surface of the reinforced concrete block 11, and a measurement unit 15 (similar to that shown in FIG. 1 although not shown in FIG. 4) connected to the acoustic transducers 14 via a signal cable 17 (similar to that shown in FIG. 1 although not shown in FIG. 4).

The plurality of acoustic transducers 14 are disposed around the coil 12, and the coil 12 is excited by applying a current pulse thereto thereby generating an acoustic wave from the reinforcing iron rod 11a. The acoustic wave is detected and converted into electric signals by the respective acoustic transducers 14, and the resultant electric signals are supplied to the measurement unit 15. The measurement unit 15 determines propagation delay times, that is, times needed for the acoustic wave to propagate from the acoustic wave source to the respective acoustic transducers 14.

The propagation velocity of the acoustic wave in the concrete 11b can be regarded to be substantially constant. Therefore, from the propagation velocity v and the delay times t, it is possible to determine, the distances r from the acoustic wave source to the respective acoustic transducer 14, that is, the distances from the reinforcing iron rod 11a to the respective acoustic transducer 14. From those distances, it is possible to determine the location of the acoustic wave source, that is, the location of the reinforcing iron rod 11a.

For example, in a case in which the reinforcing iron rod 11a has the shape of a rod such as that shown in FIG. 4, if the distances ra, rb, and rc (=v·ta, v·tb, and v·tc) from the acoustic wave source to the reinforcing iron rod 11a are determined from the propagation delay times ta, tb, and tc detected by the acoustic transducers 14a, 14b and 14c, and if spheres with radii ra, rb, and rc, respectively, are drawn so that the center of each sphere is located at the corresponding location of the acoustic transducer 14, then the location of the reinforcing iron rod 11a is given by a common point of contact of spheres.

Although in the above-described example, a plurality of acoustic transducers 14 are disposed on the surface of the concrete 11 and the propagation delay times at the locations of the acoustic transducers 14 are simultaneously measured for a single acoustic signal, the propagation delay times at various locations may be measured using a single acoustic transducer 14 in such a manner that the location of the acoustic transducer 14 is changed across the surface of the concrete 11, an acoustic signal is generated at each location and the propagation delay time is measured.

Now, a second example is described.

In this second example, an example of measurement using the acoustic diagnosis/measurement apparatus using a pulse of electromagnetic force according to the present invention is described.

Figure 5:
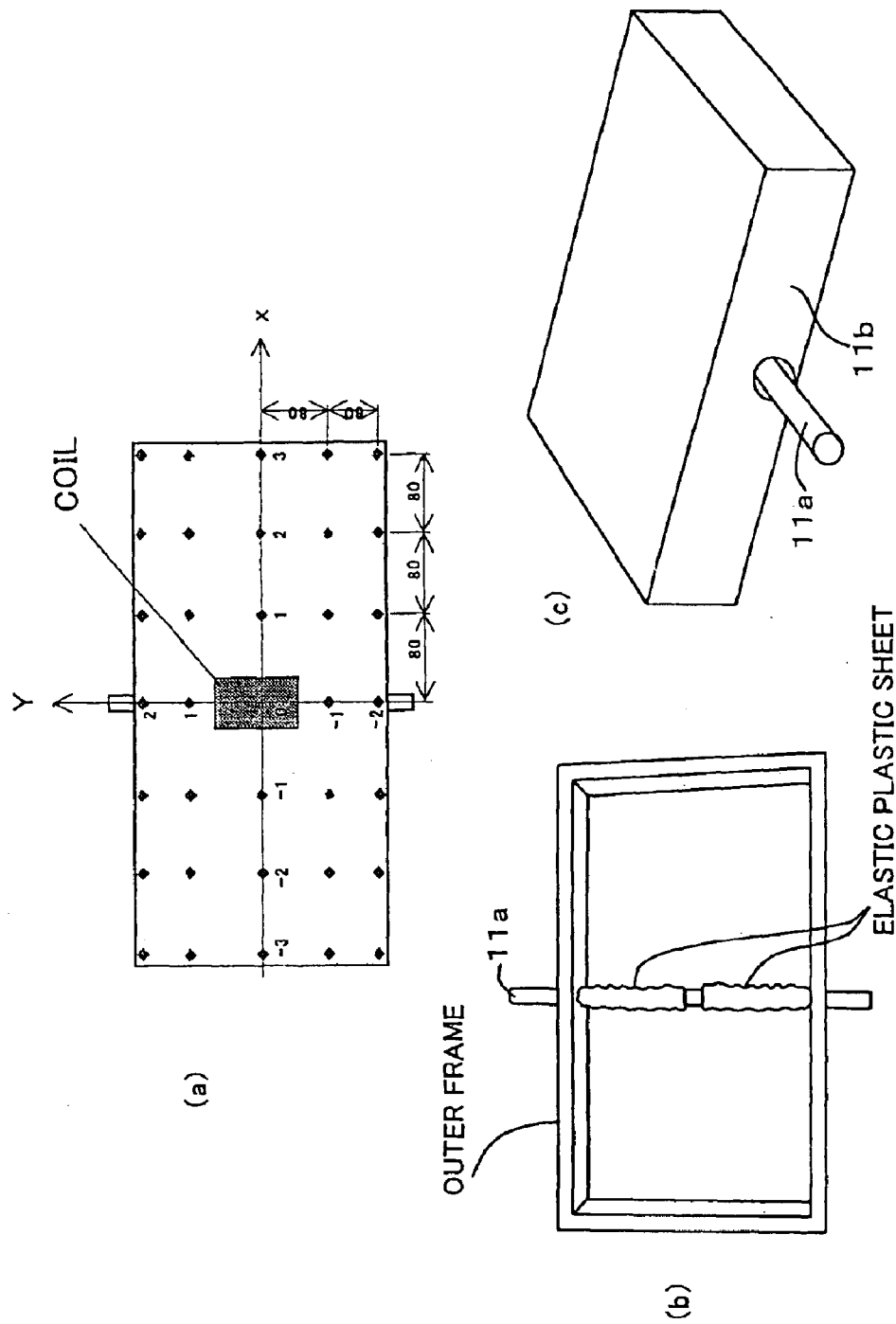

FIG. 5(a) to 5(c) show the surface shape of reinforced concrete used in an embodiment and a method of producing the reinforced concrete, wherein FIG. 5(a) shows the shape of a surface of the reinforced concrete, FIG. 5(b) shows an outer frame used to form the reinforced concrete, and FIG. 5(c) shows the external appearance of produced reinforced concrete. As shown in FIG. 5(b), the reinforced concrete used in this example was produced by pouring concrete into the outer frame, in the center of which a reinforcing iron rod 11a covered, except for its center, with an elastic plastic sheet was disposed, so that only the central portion of the reinforcing iron rod 11a was brought into contact with the concrete 11b and the other portion was not in contact with the concrete 11b. In this structure, a generated acoustic wave propagates into the concrete from the center of the reinforcing iron rod 11a, and thus the acoustic wave source can be regarded as a point source.

As shown in FIG. 5(a), the center of the reinforced concrete 11 was taken as the origin and the horizontal and vertical axes were taken as x and y axes, respectively. The coil was disposed at the origin, and the location of the acoustic transducer was represented by coordinates (x, y). The propagation delay time of the acoustic wave detected by the acoustic transducer was measured for various values of coordinates (x, y). The exciting coil, the acoustic transducer, and the current pulse used herein are similar to those used in the first example.

FIG. 6 is a diagram showing propagation delay times in the reinforced concrete, measured at different distances from the acoustic wave source.

In FIG. 6, CH1 and CH2 denote acoustic waveforms detected by the acoustic transducer placed at coordinates (−1, 0) and (3, 2), respectively, shown in FIG. 5(a), and CH3 denotes the waveform of the current pulse. The horizontal axis represents the time in units of 0.1 ms/div and the vertical axis represent the voltage corresponding to the strength of the acoustic waveforms denoted by CH1 and CH2, wherein the zero point of the voltage axis for CH1 was shifted from that for CH2.

As can be seen from FIG. 6, the acoustic waveform CH1 detected at a position near the acoustic wave source appears at substantially the same time as the current pulse rises. In contrast, the acoustic waveform CH2 detected at a position distant from the acoustic wave source appears after a rather large delay from the leading edge of the current pulse.

Thus, it is possible to detect the distance from the acoustic power source by detecting the propagation delay time.

Figure 7:
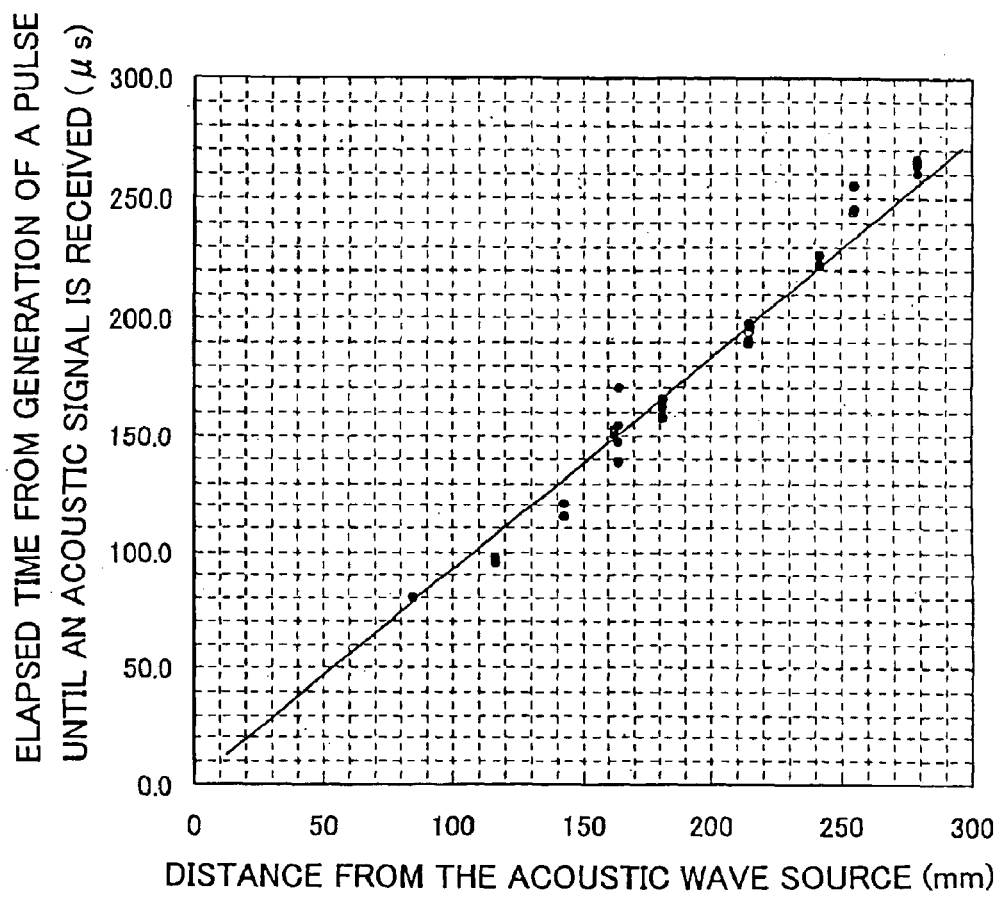
FIG. 7 is a graph showing a manner in which the velocity of an acoustic wave propagating through concrete is determined from propagation delay times measured at various distances from an acoustic wave source.

FIG. 7 is a graph showing a manner in which the velocity of an acoustic wave propagating through concrete is determined from propagation delay times measured at various distances from an acoustic wave source.

In FIG. 7, the distance from the acoustic wave source denotes the distance between each coordinate point shown in FIG. 6(a) and the acoustic wave source. The propagation delay time was measured in the same manner as described above with reference to FIG. 7.

As can be seen from FIG. 7, the velocity of the acoustic wave propagating through concrete can be regarded as constant.

Therefore, the distance to the acoustic wave source can be determined from the propagation delay time described with reference with FIG. 6 and the velocity of the acoustic wave described with reference with FIG. 7. If the distance to the acoustic wave source is measured at a large number of points, the location of the reinforcing iron rod can be given by a location which satisfies all measured distances.

As described above, the acoustic location detector using a pulse of electromagnetic force according to the present invention is capable of non-destructively detecting the location of a reinforcing iron rod.

Now, an acoustic diagnosis/measurement apparatus according to the present invention is described.

This acoustic diagnosis/measurement apparatus is similar to the acoustic diagnosis/measurement apparatus 10 except that the acoustic transducer 14 is replaced by a surface displacement detector and a surface vibration of a structure 11 to be examined is detected instead of an acoustic wave.

Although any type of detector may be employed as the surface displacement detector as long as it is capable of measuring a small displacement, it is desirable to use a laser interferometer because precise and detailed diagnosis is possible by illuminating the entire surface of the structure 11 to be diagnosed with coherent laser light and detecting an interference pattern indicating the phase difference of a reflected light caused by the surface vibration of the structure 11.

The coil and the power supply unit used in the acoustic diagnosis/measurement apparatus according to the present invention are described below.

Figure 8:
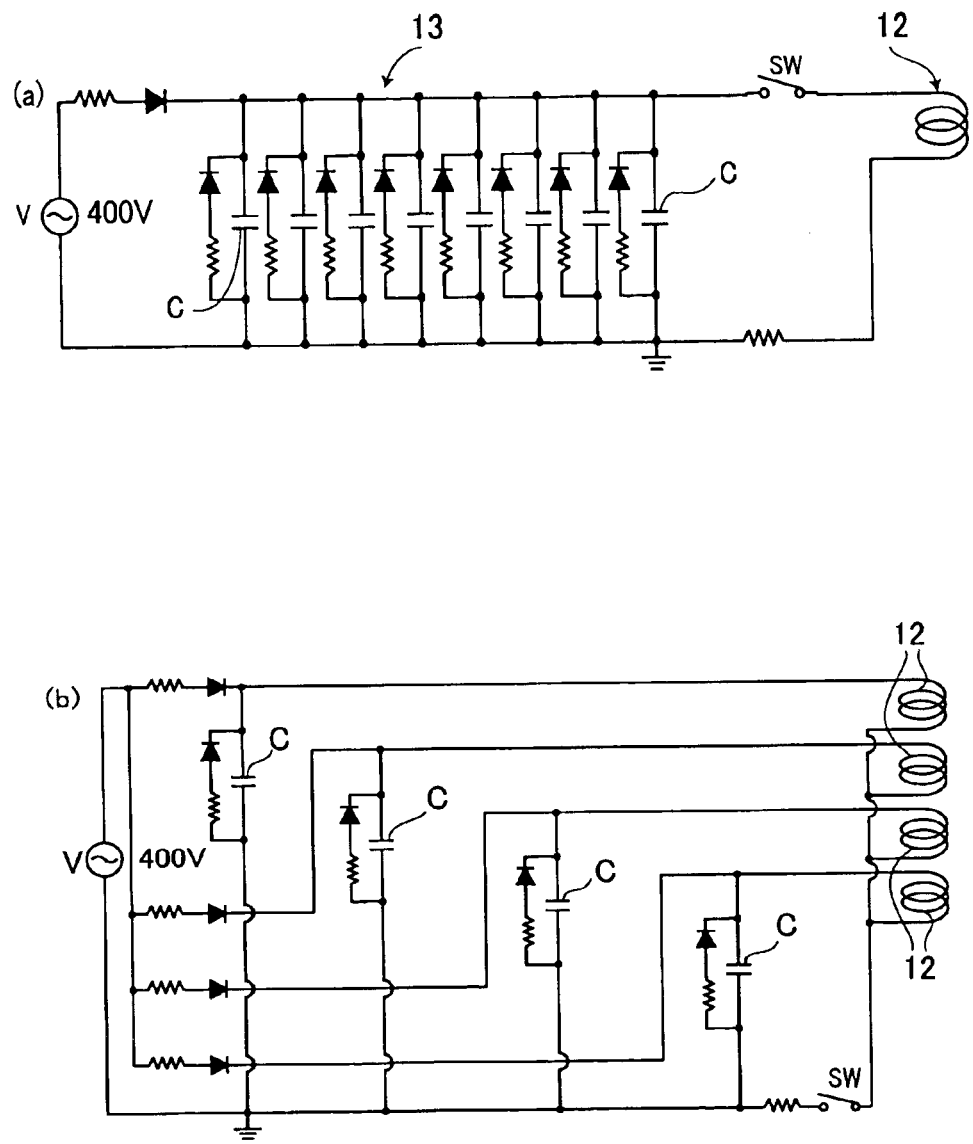
FIG. 8(a) shows a coil and a power supply unit according to a conventional technique.
FIG. 8(b) shows a coil and a power supply unit according to the present invention.

FIG. 8(a) shows a coil and a power supply unit according to a conventional technique, and FIG. 8(b) shows a coil and a power supply unit according to the present invention.

In the conventional technique, as shown in FIG. 8(a), the coil is constructed in the form of a single piece of coil, and a current pulse is applied to the coil 12 in such a manner that the capacitor C is charged by an AC voltage V supplied from commercial electric power and the charge stored in the capacitor C is transferred to the coil 12 by turning on the switch SW which may be a mechanical switch or a semiconductor switch.

On the other hand, in the present invention, as shown in FIG. 8(b) coils is divided into a plurality of subcoils 12 each having small inductance, and the subcoils 12 are disposed coaxially and closely such that magnetic fields generated by the respective coils are superimposed. A capacitor C is connected in series to each subcoil, and four series circuits each consisting of one coil 12 and one capacitor C are connected in parallel to a common power supply V via a common switch SW which may be a mechanical switch or a semiconductor switch.

In this circuit configuration, the coil in each series circuit has small inductance and the capacitor in each series circuit has small capacitance, and thus a current pulse with a small time constant can be supplied when the switch SW is turned on. The magnetic field pulses generated by the respective coils are superimposed and thus a resultant overall magnetic pulse has a small pulse width and a large crest value.

FIGS. 9(a) and 9(b) show an example of the waveform of a current pulse applied to a coil from a power source and an example of a measured acoustic signal generated thereby, wherein the example shown in FIG. 9(a) is according to a conventional technique, and the example shown in FIG. 9(b) is according to the present invention. The acoustic wave signal was measured using the acoustic diagnosis/measurement apparatus using a pulse of electromagnetic force according to the present invention. Reinforced concrete including a reinforcing iron rod 13D (deformed reinforcing iron rod with a diameter of 13 mm) with a cover depth d of 30 mm was used as a test sample. As can be seen from FIG. 9, the coil and the power supply constructed in the above-described manner according to the present invention are capable of supplying a current pulse with a much smaller pulse width and a much larger height than can be achieved by the conventional technique.

Furthermore, by employing the coil and the power supply according to the present invention, a waveform detected by the acoustic emission (AE) sensor, that is, the output waveform of the acoustic transducer becomes much greater than can be achieved by the conventional technique.

As described above, by forming the coil and the power supply in the above-described manner according to the present invention, it becomes possible to generate a magnetic field pulse with a small pulse width and a large crest value, which can strongly excite a reinforcing iron rod.

A measurement unit used in the apparatus in an embodiment of the present invention is described below.

The measurement unit according to the present invention samples the output waveform of the acoustic transducer, converts the sampled value into digital data, stores the resultant digital data into a memory, performs a particular calculation on the digital data via a CPU according to a particular signal processing program, and stores the result into a memory or displays the result on a display. The particular signal processing program includes a program of displaying a time-domain waveform of the output waveform, a program of calculating a frequency-domain waveform, that is, frequency spectrum obtained by performing a Fourier transform on the time-domain waveform of the output waveform, and other various signal processing programs which will be described later. The sampling apparatus, the analog-to-digital converter, the memory, the CPU, and the display may be those which are commercially available.

By employing the measurement unit constructed in the above described manner, it is possible to measure the waveform in the time domain and display information associated with corrosion and/or adhesion. Furthermore, it is possible to extract a feature associated with corrosion and/or adhesion from the waveform in the time domain and display the extracted feature. It is also possible to calculate the waveform in the frequency domain, that is, the Fourier transform spectrum of the output waveform, extract a feature associated with corrosion and/or adhesion from the waveform in the frequency domain, and display information associated with corrosion and/or adhesion.

Now, a third example is described below.

In this third example, it is demonstrated that a feature associated with corrosion and/or adhesion can be extracted from a waveform in the time domain.

Three different types of test blocks of reinforced concrete listed below were prepared and compared with each other.
  (A) Normal reinforced concrete.
  (B) Normal reinforced concrete was fatigued using a fatigue test machine until a slight crack starting from a reinforcing iron rod was produced.
  (C) Normal reinforced concrete was fatigued using a fatigue test machine beyond the state of the test sample (B) until adhesion between a reinforcing iron rod and concrete was lost.

The test blocks were all produced using 13D reinforcing iron rods (deformed reinforcing iron rods with a diameter of 13 mm) so as to have external dimensions of 200 mm×150 mm× and 100 mm and a cover depth d of 30 mm.

A coil 12 and an acoustic transducer 14 were attached to a surface of each test block, and a current pulse with a crest value of 2000 A and a pulse width of 350 μs was applied to each coil 12 thereby exciting the reinforcing iron rod.

Figure 10:
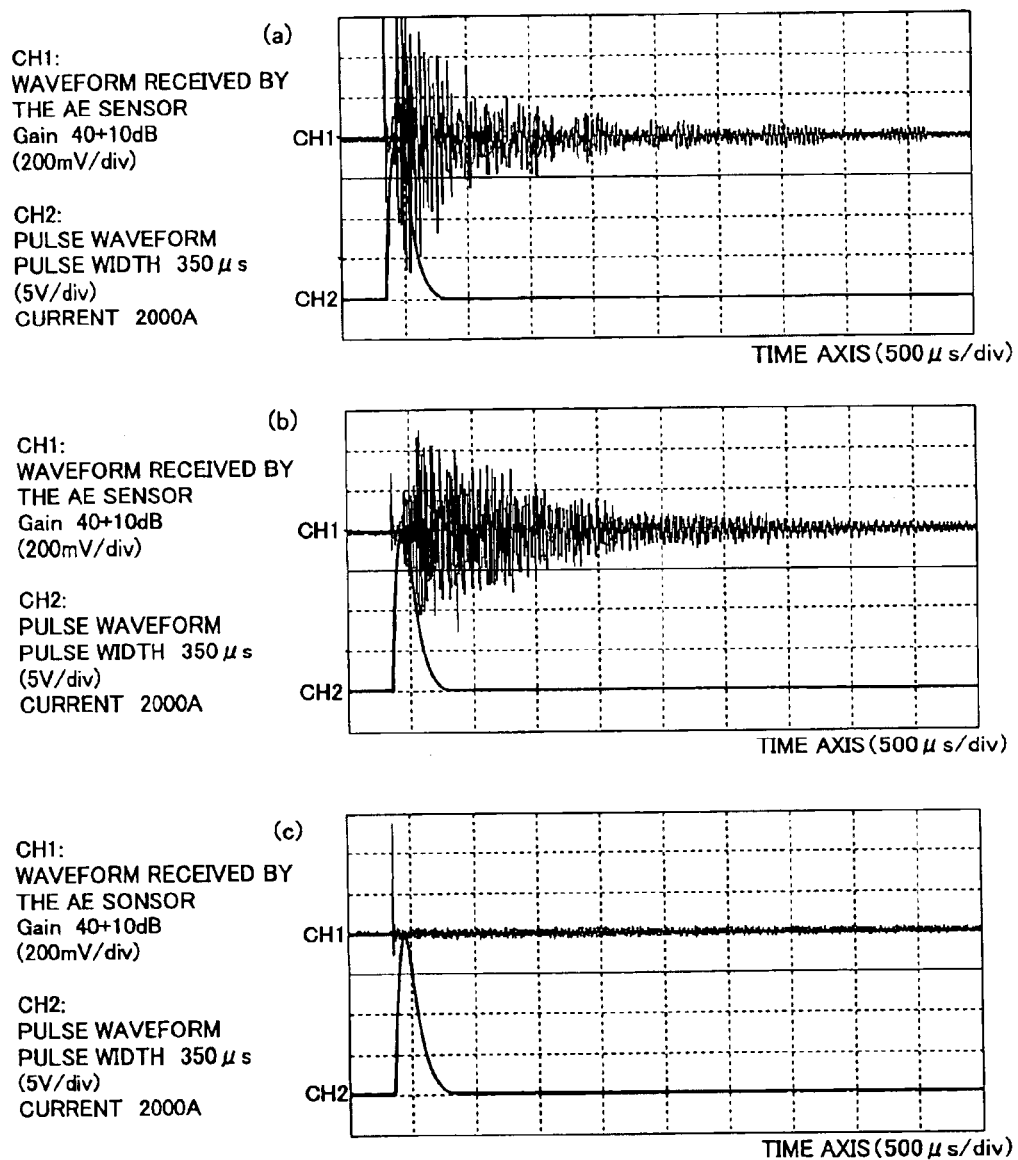
FIGS. 10(a), 10(b), and 10(c) are diagrams showing waveforms in the time domain output by the acoustic transducers attached to the respective test blocks (A), (B), and (C) and measured by the measurement unit.

FIGS. 10(a), 10(b), and 10(c) are diagrams showing waveforms in the time domain output by the acoustic transducers attached to the respective test blocks (A), (B), and (C) and measured by the measurement unit.

As can be seen from those figures, for the normal reinforced concrete block (A), a waveform having a triangle-like shape having a symmetry axis and a vertex along the time axis was obtained.

On the other hand, for the test block (B) having a crack, a waveform having a rectangle-like shape having a symmetry axis and a vertex along the time axis was obtained.

However, for the test block (C) having substantially no adhesion between the reinforcing iron rod and the concrete, substantially no output waveform was observed.

As described above, by displaying waveforms in the time domain measured by the measurement unit of the apparatus according to the present invention, it is possible to detect differences in corrosion and/or adhesion of reinforcing iron rods from the waveforms.

Now, a fourth example is described below.

In this fourth example, it is demonstrated that a feature associated with corrosion and/or adhesion can be extracted from waveforms in the time domain also in a case in which an acoustic transducer (AE sensor) is attached to an exposed part of a reinforcing iron rod of reinforced concrete as shown in FIG. 1(b).

Test blocks similar to those used in the third example were used, and an experiment was performed in a similar manner to the example 3 except for the attaching location of each acoustic transducer.

Figure 11:
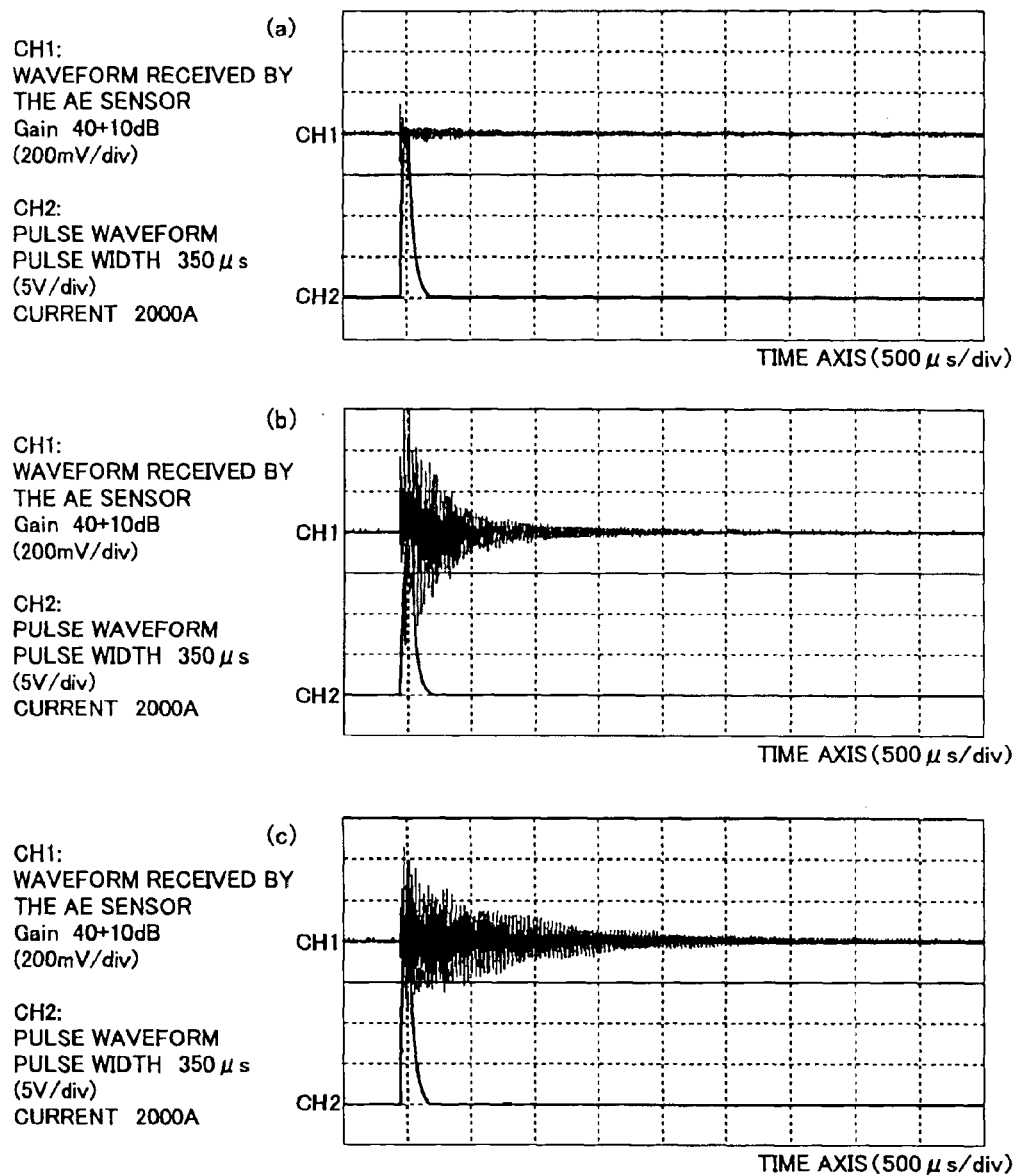
FIGS. 11(a), 11(b), and 11(c) are diagrams showing waveforms in the time domain output by the acoustic transducers directly attached to reinforcing iron rods of the respective test blocks (A), (B), and (C) and measured by the measurement unit.

FIGS. 11(a), 11(b), and 11(c) are diagrams showing waveforms in the time domain output by the acoustic transducers directly attached to reinforcing iron rods of the respective test blocks (A), (B), and (C) and measured by the measurement unit.

As can be seen from those figures, substantially no output waveform was observed for the normal reinforced concrete (A). This is because strong adhesion between the reinforcing iron rod and the concrete causes a vibration produced by exciting the reinforcing iron rod to be quickly attenuated.

On the other hand, for the test block (B) having a crack, a waveform having a triangle-like shape having a symmetry axis and a vertex along the time axis was obtained.

However, for the test block (C) having substantially no adhesion between the reinforcing iron rod and the concrete, a waveform having a triangle-like shape having a symmetry axis and a vertex along the time axis was obtained, but the waveform has a long tail extending along the time axis. This is because adhesion between the reinforcing iron rod and the concrete was lost and a space was created between the reinforcing iron rod and the concrete, and thus a vibration of the reinforcing iron rod attenuates gradually. As a result, the vibration continues for a long time.

As described above, by displaying waveforms in the time domain measured by the measurement unit of the apparatus according to the present invention, it is possible to detect differences in corrosion and/or adhesion of reinforcing iron rods from the waveforms also in the case in which the acoustic transducer is attached directly to a reinforcing iron rod.

A process, performed by the measurement unit to extract a feature associated with corrosion and/or adhesion from the shape factor or the crest factor of the waveform in the time domain and display information whether or not there is a problem associated with corrosion and/or adhesion, is described below.

First, formulas used in the signal processing program performed by the measurement unit to determine the shape factor and the crest factor are described.

Let $x_i$ denote each data value of a waveform in the time domain, and let N denote the total number of data.

An average value $x_{av}$ is defined by the following formula:

$$x_{av} = \frac{\sum_{i=1}^{N} x_i}{N}$$

An effective value $x_{rms}$ is defined by the following formula:

$$x_{rms} = \sqrt{\frac{\sum_{i=1}^{N} x_i^2}{N}}$$

A peak value $x_p$ is defined by the following formula:

$$x_p = \max_{i \in N}\{x_i\}$$

The shape factor SF is defined by the following formula:

$$SF = \frac{x_{rms}}{\overline{x}_{av}}$$

The crest factor CF is defined by the following formula:

$$CF = \frac{x_p}{x_{rms}}$$

A fifth example is described below.

In this fifth example, the shape factor SF and the crest factor CF were determined in accordance with above-described formulas (1) to (5) from the waveforms in the time domain measured in the example 3 for the respective test blocks (A), (B), and (C), and a comparison was made.

FIG. 12 is a table showing the shape factors SF and the crest factors CF for the respective test blocks (A), (B), and (C).

As can be seen from FIG. 12, the shape factor SF and the crest factor CF significantly vary depending on the test blocks, that is, depending on the adhesion of the reinforcing iron rod.

As described above, the measurement unit calculates the shape factor SF and the crest factor CF of a structure to be examined in accordance with the signal processing program and compares the calculated shape factor SF and the crest factor CF with respect to threshold values predetermined as, for example, 1.50 for the shape factor and 5.50 for the crest factor in FIG. 12. It is determined whether there is no problem depending on whether the shape factor or the crest factor of the structure under examination are greater than the corresponding threshold value, and information indicating whether or not there is a problem is displayed.

A process, performed by the measurement unit to determine a similarity factor by extracting a feature associated with corrosion and/or adhesion from the shape of the envelope curve of the waveform in the time domain and display information whether or not there is a problem associated with corrosion and/or adhesion, is described below.

First, formulas used in the signal processing program performed by the measurement unit to determine the similarity factor are described.

First, the absolute value $x_i$ is determined for each data value of the waveform in the time domain. The absolute values are put one after another in the same order as that in which the waveform was sampled, and an envelope curve which smoothly envelopes the series of the absolute values is calculated. Let $y_i$ denote each data value of the envelope curve.

A probability $P(y_i)$ is defined by the following formula:

$$P(y_i) = \frac{y_i}{\sum_{i=1}^{N} y_i}$$

Let $P_a(y_i)$ be the probability $P(y_i)$ for the structure in an initial state, and $P_b(y_i)$ be probability $P(y_i)$ for the structure used for a particular period of time, then the amount of information $IF(y_i)$ can be defined by the following formula:

$$IF(y_i) = \log \frac{P_a(y_i)}{P_b(y_i)}$$

The similarity factor SF is defined by the following formula:

$$SF = \sum_{i=1}^{N} \log \frac{P_a(y_i)}{P_b(y_i)}$$

Now, a sixth example is described below.

In this sixth example, the envelope curves were determined from the waveforms in the time domain, determined in the example 3 for the respective test blocks (A), (B), and (C), and a comparison in terms of the similarity factor was performed.

FIG. 13(a) shows the envelope curves determined for the respective test blocks (A), (B), and (C), and FIG. 13(b) shows the corresponding logarithmic inverse envelope curves. Herein, the logarithmic inverse envelope curve refers to an envelop curve for the logarithm value of the inverse of the probability $P(y_i)$.

As can be seen from FIG. 13(a), the envelope curves of the test blocks (B) and (C) are significantly different from that of the test block (A). Thus, by comparing an envelope curve such as that for the test block (B) or (C) with respect to an envelope curve in an initial state such as that for the test block (A), it is possible to detect an occurrence of corrosion and/or a reduction in adhesion.

As can be seen from FIG. 13(b), also in the logarithmic inverse envelope curves, a clear difference relative to the initial state appears, and thus the similarity factor obtained by adding the differences along the time axis is used to diagnose corrosion and/or adhesion.

As described above, in accordance with the signal processing program, the measurement unit calculates the envelope curve, the logarithmic inverse envelope curve, and the similarity factor and compares the similarity factor with the predetermined threshold value. Depending on whether the similarity factor is greater than or equal to or smaller than the threshold value, information indicating whether or not there is a problem is displayed.

The measurement unit may extract a feature associated with corrosion and/or adhesion from a normalized waveform obtained by dividing each value of a waveform in the time domain by the effective value of the waveform or from a waveform obtained by exponentiating the normalized waveform whereby information associated with the corrosion and/or adhesion may be displayed. This technique is described in further detail below.

The normalized waveform can be obtained by dividing the data value $X_i$ of the waveform in the time domain by the effective value $x_{rms}$ given by formula (2).

With reference to a seventh example, the technique is described further.

In this seventh example, the normalized waveform and the exponentiation of the waveform thereof are calculated for the respective test blocks (A), (B), and (C) from the time-domain waveforms measured in the example 3 for the respective test blocks (A), (B), and (C).

FIGS. 14(a), 14(b), and 14(c) respectively show the time-domain waveform, the normalized waveform, and the square of the normalized waveform, obtained for the test block (A).

Figure 15:
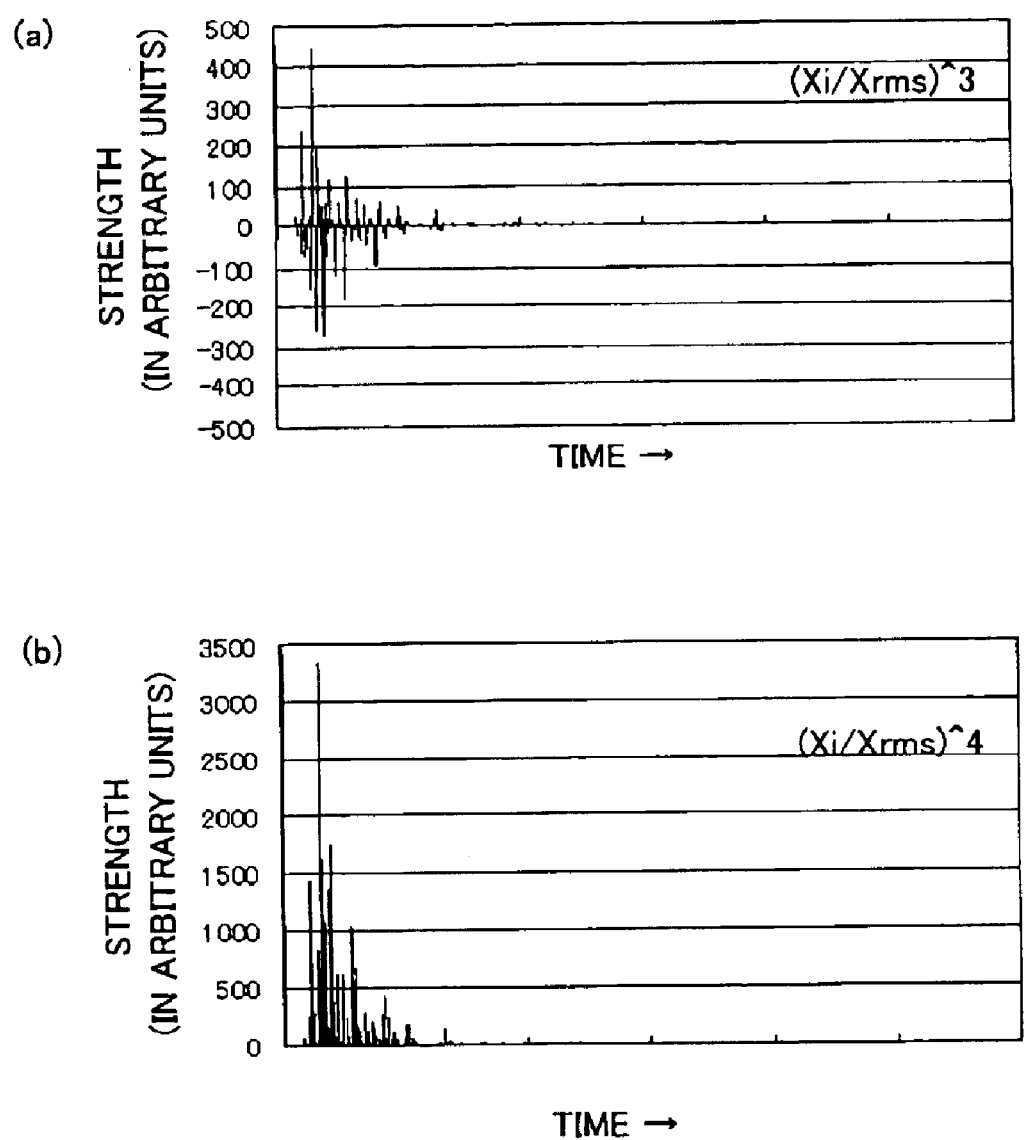

FIGS. 15(a) and 15(b) respectively show the cube and the quartic of the normalized waveform of the test block (A).

FIGS. 16(a), 16(b), and 16(c) respectively show the time-domain waveform, the normalized waveform, and the square of the normalized waveform, obtained for the test block (B).

FIGS. 17(a) and 17(b) respectively show the cube and the quartic of the normalized waveform of the test block (B).

FIGS. 18(a), 18(b), and 18(c) respectively show the time-domain waveform, the normalized waveform, and the square of the normalized waveform, obtained for the test block (C).

FIGS. 19(a) and 19(b) respectively show the cube and the quartic of the normalized waveform of the test block (C).

As can be seen from FIGS. 14 to 19, the normalized waveform and the exponentiation of the waveform thereof indicate more clearly the difference in the degree of corrosion and/or adhesion among the test blocks (A), (B), and (C) than can be indicated by the time-domain waveform. In particular, the waveforms obtained by means of a high-order exponentiation significantly differ depending on the degree of corrosion and/or adhesion.

As described above, by evaluating the normalized waveform or the exponentiation of the waveform thereof, it is possible to perform the high-sensitive detection of corrosion and/or adhesion.

As described above, in accordance with the signal processing program, the measurement unit extracts a feature by calculating the normalized waveform and the exponentiation of the waveform thereof from the time-domain waveform, determines, on the basis of comparison with threshold values, whether or not there is a problem associated with corrosion and/or adhesion, and displays the result.

The measurement unit may extract a feature associated with corrosion and/or adhesion from a frequency-domain waveform and may display information indicating whether or not there is a problem associated with corrosion and/or adhesion, as described in detail below.

The frequency-domain waveform is determined by the measurement unit by performing a Fourier transform on a time-domain waveform in accordance with the signal processing program.

With reference to an eighth example, the technique is described in further detail below.

In this eighth example, the frequency-domain waveform is determined by performing a Fourier transform on each of the time-domain waveforms determined in the third or fourth example for the test blocks (A), (B), and (C), and the resultant frequency-domain waveforms of the test blocks (A), (B), and (C) are compared with each other.

FIGS. 20(a), 20(b), and 20(c) respectively show frequency-domain waveforms of the test blocks (A), (B), and (C), determined from the time-domain waveforms determined in the third example for the test blocks (A), (B), and (C).

As can be seen from FIG. 20(a), in the case of the test block (A) of normal reinforced concrete, the frequency spectrum includes components distributed randomly and substantially continuously in a frequency range of 20 kHz to 80 kHz.

On the other hand, as can be seen from FIG. 20(b), in the case of the test block (B) of reinforced concrete having a crack, particular frequency components appear at particular intervals.

In the case of the test block (C) in which adhesion of a reinforcing iron rod was lost, as can be seen from FIG. 20(c), particular frequency components appear at particular intervals, although the tendency is not strong compared with the text block (B). Another feature of this test block (C) is that the frequency-domain waveform includes a large component near 150 kHz.

The difference between FIGS. 20(a) and 20(b), that is, between the text block (A) and the test block (B) is very great. This makes it possible to easily detect the difference even in the case in which the difference cannot be easily detected from the time-domain waveforms.

Figure 21:
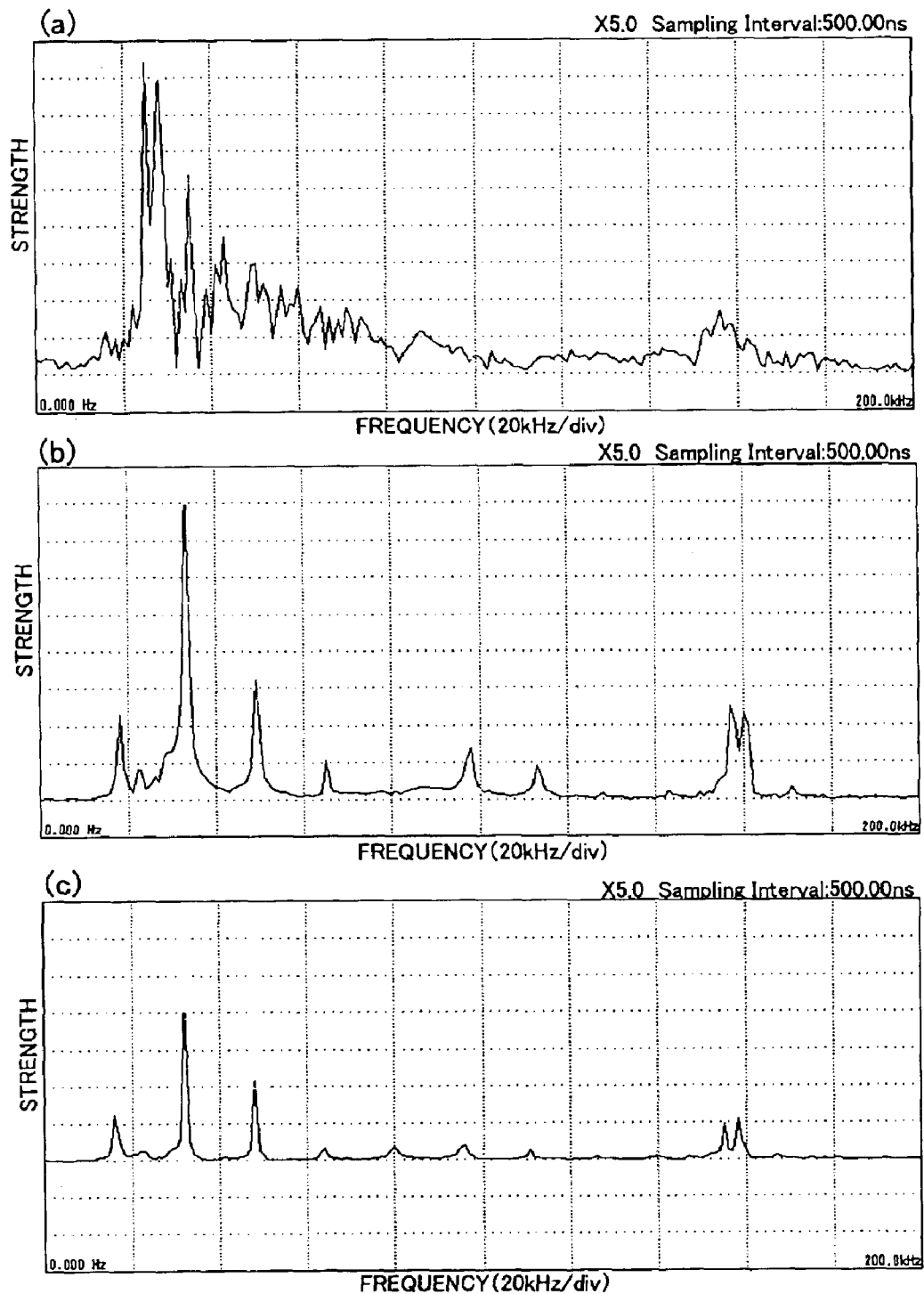
FIGS. 21(a), 21(b), and 21(c) respectively show frequency-domain waveforms of the test blocks (A), (B), and (C), determined from the time-domain waveforms determined in the fourth example for the test blocks (A), (B), and (C).

FIGS. 21(a), 21(b), and 21(c) respectively show frequency-domain waveforms of the test blocks (A), (B), and (C), determined from the time-domain waveforms determined in the fourth example for the test blocks (A), (B), and (C) by using the acoustic transducers attached directly to reinforcing iron rods.

Figure 20:
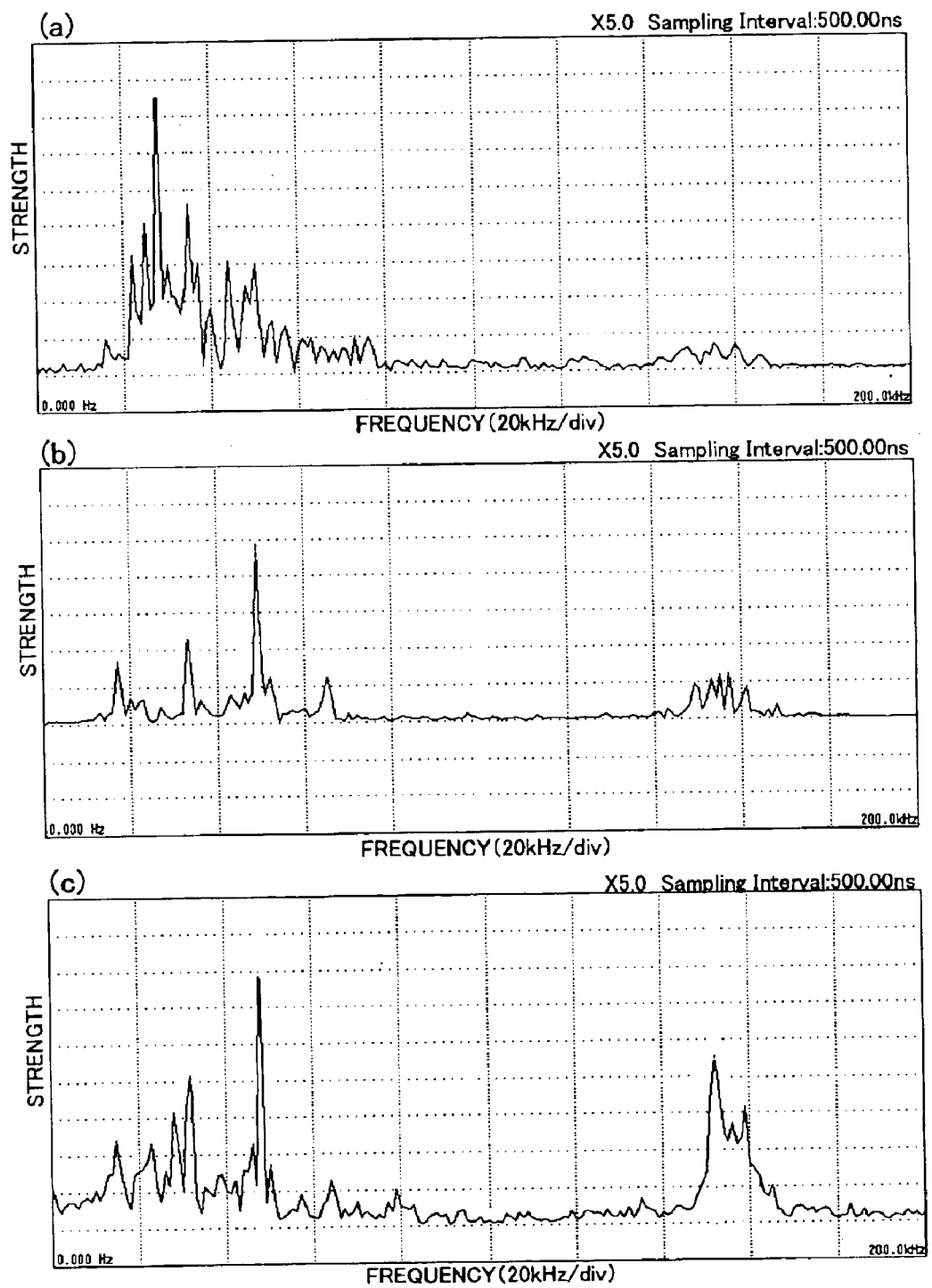
FIGS. 20(a), 20(b), and 20(c) respectively show frequency-domain waveforms of the test blocks (A), (B), and (C), determined from the time-domain waveforms determined in the third example for the test blocks (A), (B), and (C).

As can be seen from those figures, in the case in which the acoustic transducers are directly attached to reinforcing iron rods, particular frequency components appear at particular intervals with decreasing adhesion, as in the case shown in FIG. 20.

As described above, in accordance with the signal processing program, the measurement unit calculates the frequency-domain waveform from a time-domain waveform and compares the resultant frequency-domain waveform with a reference pattern thereby determining the similarity. The similarity is then compared with a threshold value of similarity. Depending on whether the similarity is equal to or smaller than the threshold value, it is determined whether or not there is a problem, and information indicating the result is displayed.

The measurement unit may determine the normalized waveform or the exponentiation of the normalized waveform from a frequency-domain waveform in a similar manner as described above with reference to the sixth or seventh example, and may perform a high-sensitive extraction of a feature associated with corrosion and/or adhesion using the normalized waveform or the exponentiation of the normalized waveform. Furthermore, the similarity factor may be calculated from the normalized waveform or the exponentiation of the normalized waveform, and the resultant similarity factor may be compared with a predetermined threshold value thereby performing a high-sensitive detection of whether the similarity factor of a structure under examination is equal to or smaller than the threshold value. In accordance with the result, information indicating whether or not there is a problem is displayed.

A method of measuring the cover depth of reinforced concrete or the diameter of a reinforcing iron rod according to the present invention is described below.

FIG. 22(a) is a diagram showing a method of measuring the diameter or the cover depth of a reinforcing iron rod according to the present invention, and FIG. 22(b) is a graph showing a measurement result.

As described in FIG. 22(a), a coil 12 is attached to a surface of reinforced concrete 11, at a location exactly above a reinforcing iron rod 11a, and an acoustic transducer 14 is attached to the surface of the reinforced concrete 11. The reinforcing iron rod 11a is then excited by a magnetic field pulse generated by the coil 12, thereby generating an acoustic signal from the reinforcing iron rod 11a. The acoustic signal is converted into an electric signal by the acoustic transducer 14 and supplied to a measurement unit 15. The measurement unit 15 extracts a feature value such as the peak-to-peak value of the crest value of the acoustic signal. If the cover depth d is known, the diameter of the reinforcing iron rod can be determined from the extracted feature value and the cover depth d on the basis of the predetermined correspondence among the feature value, the diameter of reinforcing iron rod, and the cover depth. In a case in which the cover depth d is unknown, the cover depth d can be determined in accordance with the technique disclosed in claim 2 of the present invention.

In a case in which the diameter of the reinforcing iron rod is known but the cover depth d is unknown, the cover depth d is determined from the detected feature value and the diameter of the reinforcing iron rod on the basis of the predetermined correspondence among the feature value, the diameter of the reinforcing iron rod, and the cover depth.

In FIG. 22(b), the vertical axis represents the feature value. In this specific example, the peak-to-peak value of the crest value is employed as the feature value. The horizontal axis represents the cover depth d. As shown in an insertion in FIG. 22(b), the dependence of the feature value on the cover depth d was determined for various diameters of the reinforcing iron rods 10d, 13d, 16d, 19d, and 25d (deformed reinforcing iron rods with diameters of 10 mm, 13 mm, 16 mm, 19 mm, and 25 mm).

As can be seen from FIG. 22(b), the feature value depends on both the diameter of the reinforcing iron rod and the cover depth d. Thus, on the basis of the dependence determined above, it is possible to determine the cover depth d or the diameter of the reinforcing iron rod.

A method of diagnosing/measuring whether a binding member is securely fastened according to claim 19 of the present invention is described below.

Figure 23:
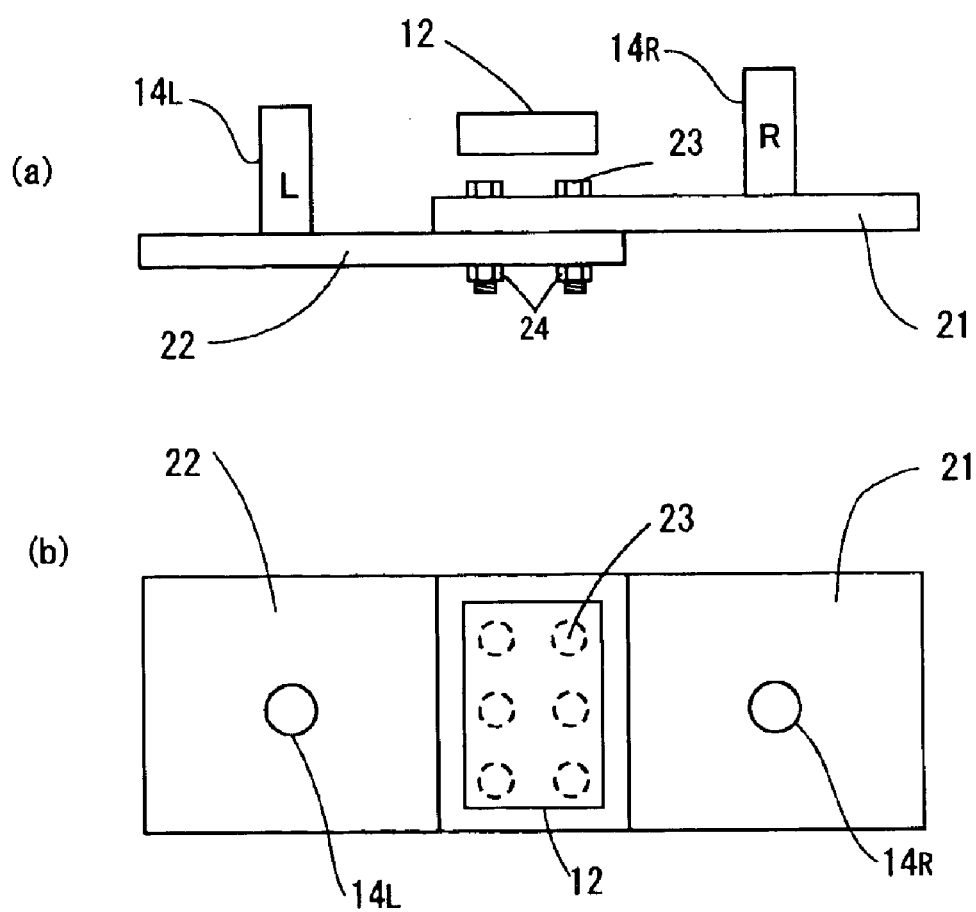

FIGS. 23(a) and 23(b) are diagrams showing a method of diagnosing or measuring the secureness of a binding member, according to the present invention, wherein FIG. 23(a) is a side view of a conductor 21 and a conductor 22 bound together via a bolt 23 and a nut 24, and FIG. 23(b) is a plan view thereof.

A coil 12 is disposed exactly above the bolt 22 binding the conductor 21, and acoustic transducers 14R and 14L are attached to the surfaces of the respective conductors 21 and 22. If a magnetic filed pulse is generated by the coil 12, an eddy current is induced in the surface of the conductor 21 and a magnetic field generated by the eddy current interacts with the magnetic field of the magnetic field pulse whereby the conductor 21 is oscillated. If the bolt 23 and the nut 24 are screwed in a securely fastened state, an acoustic signal generated in the conductor 21 propagates to the conductor 22 without having a significant attenuation and thus acoustic signals detected by the acoustic transducer 14R and the acoustic transducer 14L become nearly equal in magnitude. However, if the bolt 23 and the nut 24 are screwed in a loose state, an acoustic signal generated in the conductor 21 does not propagate easily into the conductor 22, and thus a difference occurs between acoustic signals detected by the acoustic transducer 14R and the acoustic transducer 14L.

Thus, it is possible to evaluate whether binding members are in a securely fastened state.

A ninth example is described below.

In this ninth example 9, it is demonstrated that the fastening state of binding members can be evaluated using the method of diagnosing/measuring a fastening state of a binding member according to the present invention.

Two aluminum plates (200×300×3t) were bound with six sets of stainless steel bolts ad nuts (M10×15). A current pulse with a crest value of 2000 A and a pulse width of 350 $\mu$s was applied to the coil.

FIGS. 24(a) to 24(d) shows a measurement result obtained when the bolts and nuts were in a securely fastened state, wherein FIGS. 24(a) and 24(b) show output waveforms of the acoustic transducer 14R attached to the conductor 21 facing the coil, and FIGS. 24(c) and 24(d) show output waveforms of the acoustic transducer 14L attached to the conductor 22 bound with the conductor 21 using the bolts and nuts.

Note that FIGS. 24(a) and 24(c) show waveforms obtained by passing the original output waveforms of the acoustic transducer through a bandpass (BP) filter (having a passband of 20 kHz to 500 kHz) thereby removing frequency components lower than 20 kHz, while FIGS. 24(b) and 24(d) show waveforms including whole frequency components up to 500 kHz.

As can be seen from those figures, when the bolt and the nut are securely fastened, the output waveform of the acoustic transducer 14L is substantially equal to that of the acoustic transducer 14R.

Figure 25:
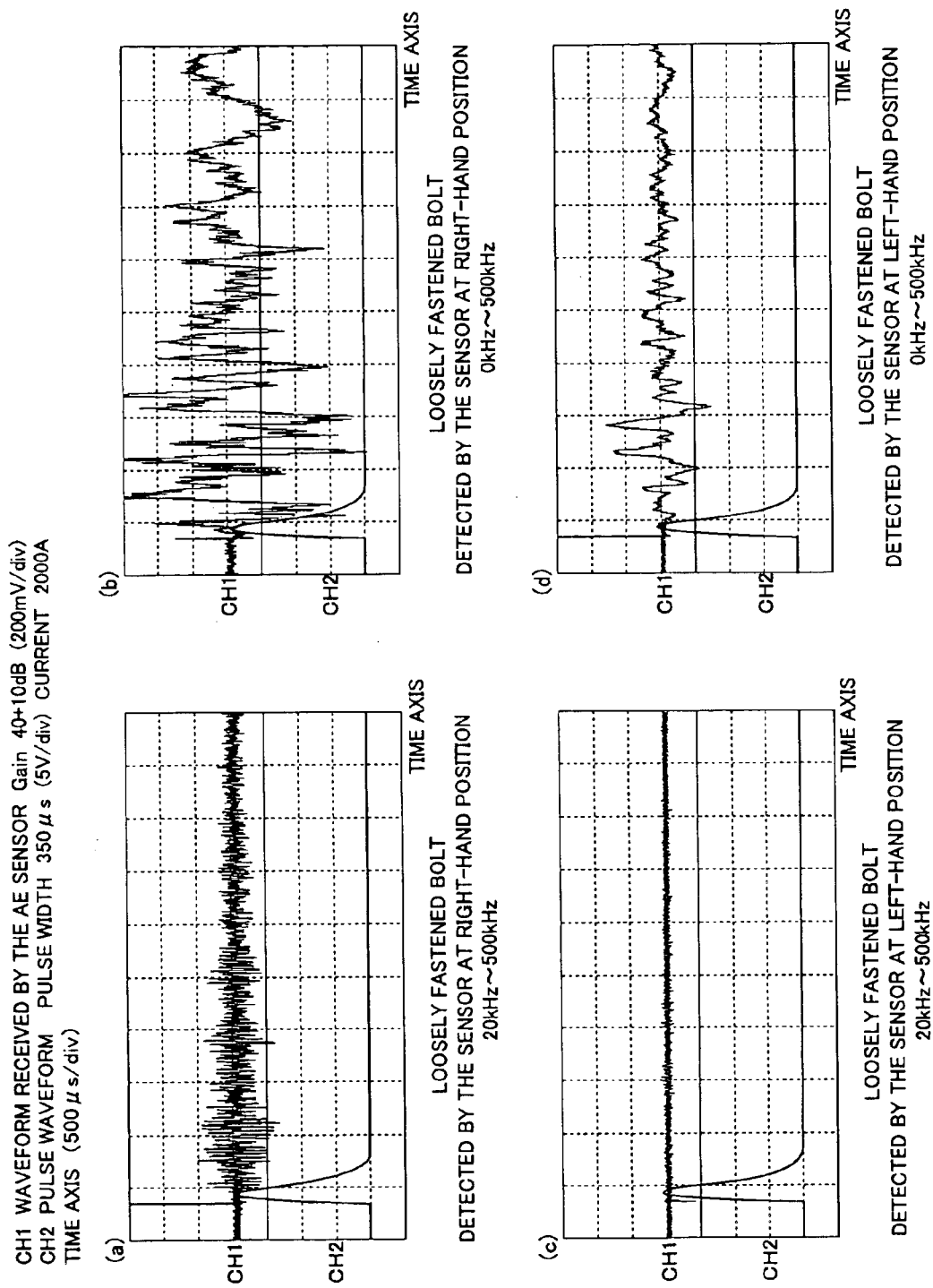

FIGS. 25(a) to 25(d) are diagrams showing a measurement result obtained when the bolt and the nut are in a loosely coupled state, wherein FIGS. 25(a) and 25(b) show output waveforms of the acoustic transducer 14R attached to the conductor 21 located closer to a coil, and FIGS. 25(c) and 25(d) show output waveforms of the acoustic transducer 14L attached to the conductor 22 bound with the conductor 21 by the bolt and the nut. Note that FIGS. 25(a) and 25(c) show waveforms obtained by passing the original output waveforms of the acoustic transducer through a bandpass (BP) filter (having a passband of 20 kHz to 500 kHz) thereby removing frequency components lower than 20 kHz, while FIGS. 25(b) and 25(d) show waveforms including whole frequency components up to 500 kHz.

As can be seen from those figures, when the bolt and the nut are not securely fastened, the output waveform of the acoustic transducer 14L is smaller in amplitude than that of the acoustic transducer 14R.

As described above, this method of the present invention makes it possible to diagnose or measure whether a binding member is securely fastened.

This method can also be used to detect a crack in a honeycomb structure used in a bridge or the like. Furthermore, the method can also be used to determine whether connection is well welded.

A method of measuring the location of a conductor embedded in a non-conductive material according to the present invention is described below.

Figure 26:
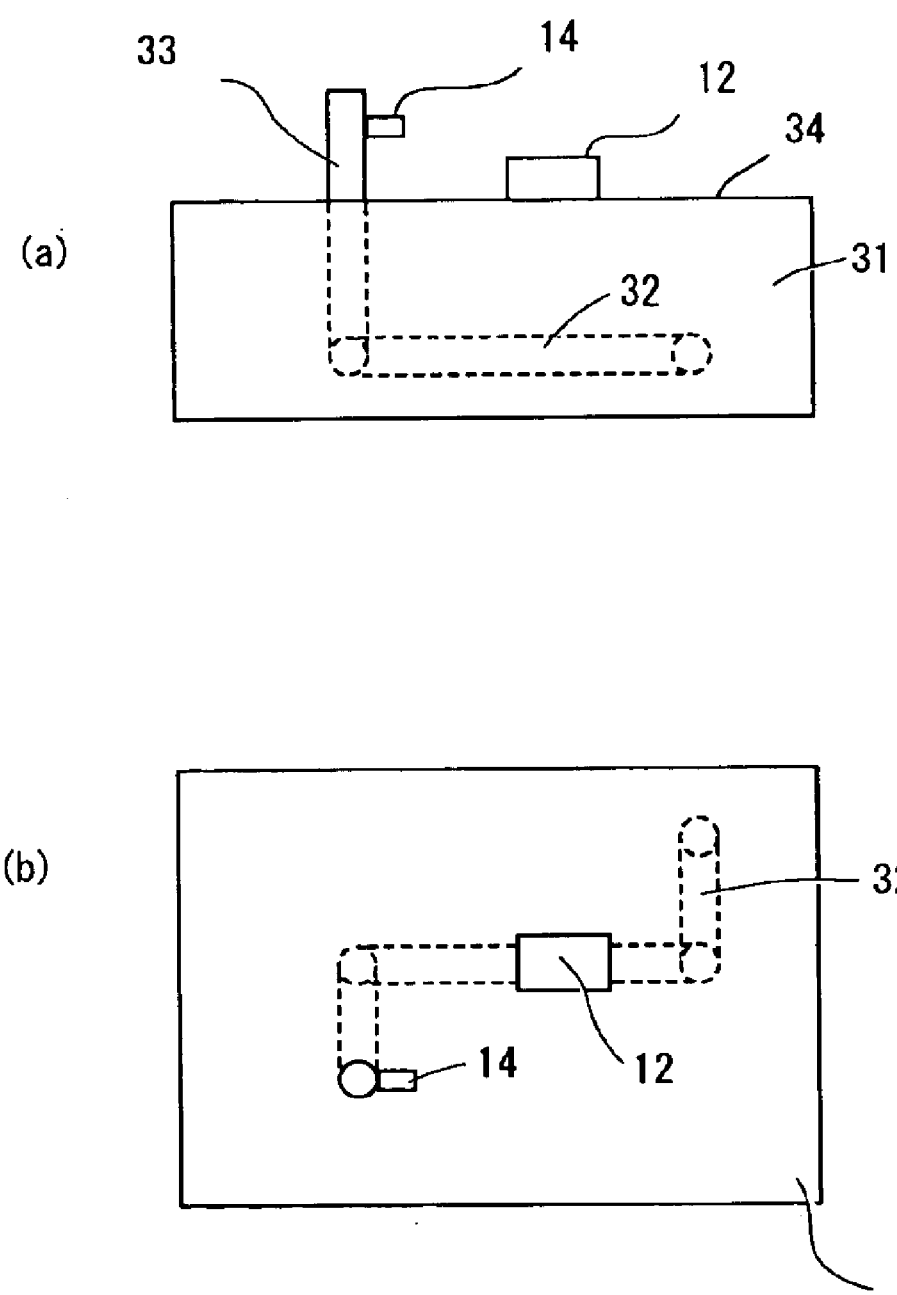

FIGS. 26(a) and 26(b) are diagrams showing a method of measuring the location of a conductor embedded in a non-conductive material, wherein FIG. 26(a) is a side view showing a manner in which an acoustic transducer 14 is attached to an exposed part 33 of a water pipe 32 buried in the ground 31 which is non-conductive, and a coil 12 is disposed on the surface 34 of ground 31, and FIG. 26(b) is a plan view thereof.

If a magnetic field pulse is generated by the coil 12, an eddy current is induced in the surface of the water pipe 32, and the water pipe 32 is oscillated as a result of interaction between the magnetic field associated with the eddy current and the magnetic field of the magnetic field pulse. An acoustic wave generated by the oscillation of the water pipe 32 propagates to the exposed part 33 of the water pipe 32 and is detected by the acoustic transducer 14. The strength of the acoustic signal becomes highest when the coil 12 is put at a location exactly above the water pipe 32. By changing the location of the coil 12 and looking for a location at which the strength of the acoustic signal becomes highest, the location of the water pipe 32 can be detected.

Now, a tenth example is described.

In this tenth example, it is demonstrated that the location of a conductor embedded in a non-conductive material can be detected by the above-described method according to the present invention.

FIGS. 27(a) to 27(c) are graphs showing results of measurement of the location of a water pipe buried in the ground, wherein FIG. 27(a) shows the waveform of an acoustic signal detected by the coil disposed exactly above the water pipe, FIG. 27(b) shows a waveform detected by the coil located 60 mm apart from the location exactly above the water pipe, FIG. 27(c) shows a waveform detected by the coil located 180 mm apart from the location exactly above the water pipe.

As can be seen from those figures, the strength of the acoustic signal becomes highest when the coil is located exactly above the water pipe, the strength of the acoustic signal decreases with the distance between the coil and the position exactly above the water pipe. Thus, if the location of the coil is changed and the location at which the acoustic signal becomes highest is determined, the location of the water pipe must be exactly below the location at which the acoustic signal becomes highest.

A method of determining whether a conductor embedded in a non-conductive material has a fracture and/or determining the location of such a fracture according to the present invention is described below.

Figure 28:
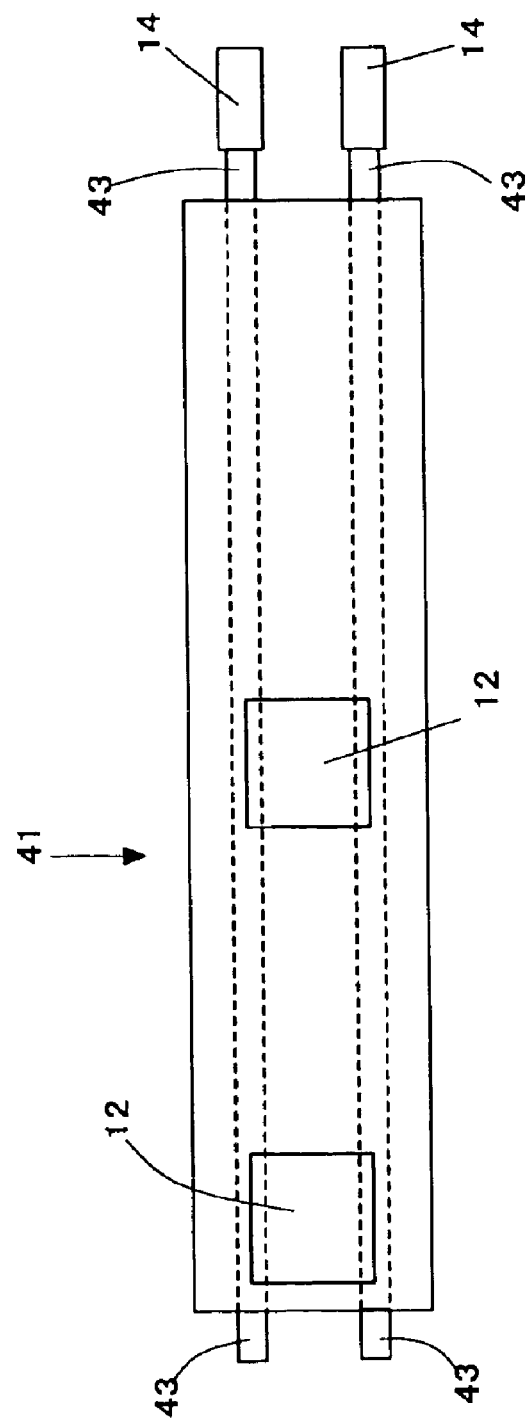
FIG. 28 is a diagram showing a method of diagnosing whether a conductor embedded in a non-conductive material has a fracture and a method of measuring the location of the fracture.

FIG. 28 is a diagram showing a method of diagnosing whether a conductor embedded in a non-conductive material has a fracture and a method of measuring the location of the fracture.

An acoustic transducer 14 is attached to an exposed part 43 of a reinforcing iron rod 42 embedded in reinforced concrete 41 with an elongated shape. A coil 12 is attached to a surface of the elongated reinforced concrete 41. An eddy current is induced in the surface of a reinforcing iron rod by generating a magnetic field pulse from the coil 12. As a result, the reinforcing iron rod 42 is excited by the interaction between the magnetic field associated with the eddy current and the magnetic field of the magnetic field pulse. An acoustic wave is generated by the excited reinforcing iron rod 42 and propagates through the reinforcing iron rod 42. The acoustic wave propagating through the reinforcing iron rod 42 is detected by the acoustic transducer 14 attached to the exposed part 43 of the reinforcing iron rod 42. If the reinforcing iron rod 42 has a fracture at some location 44, the strength of the detected acoustic signal is small, and thus the reinforcing iron rod 42 can be regarded as having a fracture. By changing the location of the coil 12 across the surface of the elongated reinforced concrete 41 and detecting a position at which the acoustic signal abruptly becomes strong, the location 44 of the fracture can be determined.

As described above, the present invention makes it possible to determine whether a reinforcing iron rod has a fracture and further determine the location of such a fracture.

Although the present invention has been described above with reference to specific embodiments, the invention is not limited to those embodiments but various modifications, additions, and eliminations are possible without departing from the spirit and the scope of the invention. It should be understood that the scope is defined by the claims appended hereto.

Industrial Applicability

According to the present invention, as described above, a conductor in a structure including the conductor and a non-conductive material covering the conductor can be directly and strongly excited by a pulse of electromagnetic force. Thus, for example, when a reinforcing iron rod in reinforced concrete is excited, a very large acoustic signal, which is influenced by corrosion and/or adhesion of the reinforcing iron rod, is obtained. This makes it possible to non-destructively and precisely diagnose/measure the location, corrosion, adhesion strength, and/or rust of the reinforcing iron rod and further a separation or a crack of the concrete, regardless of the thickness of the concrete and regardless of the degree of degradation.

Therefore, it becomes possible to diagnose/measure, very easily in a highly reliable fashion, a structure made of reinforced concrete such as a tunnel, a bridge, a building, retaining wall, dam, and civil engineering construction, thereby making it possible to perform maintenance/management of the structure made of reinforced concrete in a highly reliable fashion.

Furthermore, according to the method of acoustic diagnosis/measurement using a pulse of electromagnetic force of the present invention, it is possible to measure the cover depth of a reinforcing iron rod and/or the diameter of reinforcing iron rod. Furthermore it is also possible to determine whether a binding member such as a set of a bolt and a nut is securely fastened. The location of a water pipe or a gas pipe buried in the ground can also be detected. It is also possible to determine whether a reinforcing iron rod has a fracture. Such diagnosis/measurement can be performed easily and in a highly reliable fashion.

What is claimed is:

1. An acoustic diagnosis/measurement apparatus using a pulse of electromagnetic force, comprising a coil attached to a surface of a structure including a conductor and a non-conductive material covering the conductor; a power supply unit for supplying a current pulse to the coil; an acoustic transducer attached to the surface of the structure or to a part of the conductor, the part being separated from the non-conductive material; and a measurement unit for measuring an output waveform of the acoustic transducer, wherein corrosion of the conductor and/or adhesion strength of the conductor are diagnosed or measured, wherein the non-conductive material is concrete.

2. An acoustic diagnosis/measurement apparatus using a pulse of electromagnetic force, comprising: a coil attached to a surface of a structure including a conductor and a non-conductive material covering the conductor; a power supply unit for supplying a current pulse to the coil; and a displacement detector for optically measuring displacement of the surface of the structure thereby measuring a vibration of the surface of the structure, wherein corrosion of the conductor, and/or adhesion strength of the conductor are diagnosed or measured, wherein the non-conductive material is concrete.

3. An acoustic diagnosis/measurement apparatus using a pulse of electromagnetic force, according to claim 1 or 2, wherein the acoustic diagnosis/measurement apparatus using a pulse of electromagnetic force includes a plurality of subcoils, the plurality of subcoils being disposed coaxially such that adjacent subcoils are in close contact with each other; and the power supply unit includes charge storage capacitors connected in series to the respective coils and a power source connected, via a common switch and in parallel, to each series connection of one coil and one capacitor whereby a current pulse is applied to coils by turning on the switch thereby generating a magnetic field pulse.

4. An acoustic diagnosis/measurement apparatus using a pulse of electromagnetic force, according to claim 1 or 2, wherein a magnet for generating a static magnetic field is added to the coil.

5. An acoustic diagnosis/measurement apparatus using a pulse of electromagnetic force, according to claim 1 or 2, wherein the acoustic transducer is an element for converting an acoustic signal into an electric signal, selected from a group consisting of an acoustic emission sensor, an acceleration sensor, and a microphone.

6. An acoustic diagnosis/measurement apparatus using a pulse of electromagnetic force according to claim 1, wherein the measurement unit for measuring the output waveform measures the output waveform in the time domain, displays the measured output waveform, extracts a feature associated with corrosion and/or adhesion from the waveform in the time domain, and displays the extracted feature.

7. An acoustic diagnosis/measurement apparatus using a pulse of electromagnetic force according to claim 6, wherein the feature extracted from the waveform in the time domain is a pattern, a shape factor, or a crest factor of the waveform in the time domain; and the displaying of information associated with the corrosion and/or adhesion includes comparing the form factor or the crest factor with a predetermined threshold value and displaying whether or not there is a problem in terms of the corrosion and/or the adhesion.

8. An acoustic diagnosis/measurement apparatus using a pulse of electromagnetic force according to claim 6, wherein the feature extracted from the waveform in the frequency domain is a waveform pattern in the frequency domain; and the displaying of information associated with the corrosion and/or adhesion includes comparing the waveform pattern with a predetermined pattern, and displaying whether or not there is a problem in terms of the corrosion and/or the adhesion.

9. An acoustic diagnosis/measurement apparatus using a pulse of electromagnetic force according to claim 6, wherein the feature extracted from the waveform in the frequency domain is a normalized waveform obtained by dividing each value of the waveform in the frequency domain by the effective value of the waveform in the frequency domain or a waveform obtained by exponentiating the normalized waveform; and the displaying of information associated with the corrosion and/or adhesion includes extracting the similarity factor from the envelope curve of the normalized waveform, comparing the similarity factor with a predetermined threshold value, and displaying whether or not there is a problem in terms of the corrosion and/or the adhesion.

10. An acoustic diagnosis/measurement apparatus using a pulse of electromagnetic force according to claim 2, wherein the displacement detector is a laser interferometer for illuminating a surface of the structure with a coherent laser beam and detecting a phase difference as an interference pattern of a reflected laser beam, the phase difference varying depending on a vibration of a surface of the structure.

11. An acoustic diagnosis/measurement apparatus using a pulse of electromagnetic force, comprising a coil attached to a surface of a structure including a conductor and a non-conductive material covering the conductor; a power supply unit for supplying a current pulse to the coil; and acoustic transducer attached to the surface of the structure or to a part of the conductor, the part being separated from the non-conductive material; and a measurement unit of measuring an output waveform of the acoustic transducer in the time domain, displays the measured output waveform in the time domain, extracts a feature associated with corrosion and/or adhesion from the waveform in the time domain, and displays the extracted feature, wherein the extracted feature is a similarity factor extracted from the shape of the envelope curve of the waveform in the time domain and the displaying of information associated with the corrosion and/or adhesion includes comparing the similarity factor with a predetermined threshold value and displaying whether or not there is a problem in terms of the corrosion and/or the adhesion.

12. An acoustic diagnosis/measurement apparatus using a pulse of electromagnetic force, comprising a coil attached to a surface of structure including a conductor and a non-conductive material covering the conductor; a power supply unit for supplying a current pulse to the coil; an acoustic transducer attached to the surface of the structure or to a part of the conductor, the part being separated from the non-conductive material; and a measurement unit for measuring an output waveform of the acoustic transducer in the time domain, wherein the measurement unit measures the output waveform in the time domain, displays the measured output waveform in the time domain, extracts a feature associated with corrosion and/or adhesion from the waveform in the time domain, and displays the extracted feature, wherein the extracted feature is a waveform obtained by the exponentiation of a normalized waveform which is obtained by dividing each value of the waveform in the time domain by the effective value of the waveform in the time domain.

13. An acoustic diagnosis/measurement apparatus using a pulse of electromagnetic force according to claim 12, wherein a similarity factor is extracted from the envelope curve of the normalized waveform and compared with a predetermined threshold value, and information indicating whether or not there is a problem in terms of the corrosion and/or the adhesion is displayed.

14. A method of acoustic diagnosis/measurement using a pulse of electromagnetic force, comprising the steps of: attaching a coil to a surface of a structure including a conductor and a non-conductive material covering the conductor; applying a current pulse to the coil thereby generating magnetic field pulse; inducing an eddy current in the conductor by the magnetic field pulse; oscillating the conductor by interaction between the eddy current and the magnetic field pulse thereby generating an acoustic wave; converting an acoustic signal of the acoustic wave into an electric signal by using an acoustic transducer attached to the surface of the structure or attached to a part of the conductor, the part of the conductor being separated from the non-conductive material; and measuring the waveform of the electric signal to perform diagnosis and/or measurement in terms of corrosion and/or adhesion of the conductor, wherein the non-conductive material is concrete.

15. A method of acoustic diagnosis/measurement using a pulse of electromagnetic force, comprising the steps of: attaching a coil to a surface of a structure including a conductor and a non-conductive material covering the conductor; applying a current pulse to the coil thereby generating a magnetic field pulse; inducing an eddy current in the conductor by the magnetic field pulse; oscillating the conductor by interaction between the eddy current and the magnetic field pulse thereby generating an acoustic wave; detecting an optical displacement corresponding to a surface vibration of the structure generated by the acoustic wave thereby diagnosing the location of the conductor and the state of the structure, wherein the non-conductive material is concrete.

16. An acoustic diagnosis/measurement apparatus using a pulse of electromagnetic force, comprising a coil attached to a surface of a structure including a conductor made of magnetic material and a non-conductive material covering the conductor; a power supply unit for supplying a current pulse to the coil; an acoustic transducer attached to the surface of the structure or to a part of the conductor, the part being separated from the non-conductive material; and a measurement unit for measuring an output waveform of the acoustic transducer, wherein the conductor made of magnetic material is further oscillated than a conductor made of non-magnetic material by a force associated with magnetic energy of the conductor made of magnetic material, and corrosion of the conductor made of magnetic material and/or adhesion strength of the conductor made of magnetic material are diagnosed or measured, wherein the non-conducive material is concrete.

17. An acoustic diagnosis/measurement apparatus using a pulse of electromagnetic force, comprising: a coil attached to a surface of a structure including a conductor made of magnetic material and a non conductive material covering the conductor; a power supply unit for supplying a current pulse to the coil; and a displacement detector for optically measuring displacement of the surface of the structure thereby measuring a vibration of the surface of the structure, wherein the conductor made of magnetic material is further oscillate than a conductor made of non-magnetic material by a force associated with magnetic energy of the conductor made of magnetic material, and corrosion and/or adhesion strength of the conductor made of magnetic material are diagnosed or measured wherein the non-conductive material is concrete.

18. An acoustic diagnosis/measurement apparatus using a pulse of electromagnetic force, according to claim 16 or 17, wherein the conductor made of magnetic material is an iron rod and the non-conductive material covering the conductor is concrete.

19. A method of acoustic diagnosis/measurement using a pulse of electromagnetic force, comprising the steps of: attaching a coil to a surface of a structure including a conductor made of magnetic material and a non-conductive material covering the conductor; applying a current pulse to the coil thereby generating a magnetic field pulse; inducing an eddy current in the conductor made of magnetic material by the magnetic field pulse; oscillating the conductor made of magnetic material by interaction between the eddy current and the magnetic field pulse thereby generating an acoustic wave, wherein the conductor made of magnetic material is further oscillated than a conductor made of non-magnetic material by a force associated with magnetic energy of the conductor made of magnetic material; converting an acoustic signal of the acoustic wave into an electric signal by using an acoustic transducer attached to the surface of the structure or attached to a part of the conductor made of magnetic material, the part of the conductor made of magnetic material being separated from the structure; and measuring the waveform of the electric signal to perform diagnosis and/or measurement in terms of corrosion and/or adhesion of the conductor made of magnetic material, wherein the non-conductive material is concrete.

20. A method of acoustic diagnosis/measurement using a pulse electromagnetic force, according to claim 19, wherein the conductor made of magnetic material is an iron rod and the non-conductive material covering the conductor is concrete.

* * * * *